(12) United States Patent
Benedict

(10) Patent No.: US 11,608,788 B2
(45) Date of Patent: Mar. 21, 2023

(54) FUEL QUALITY INDICATOR

(71) Applicant: OHNOH2O, LLC, Lake Worth, FL (US)

(72) Inventor: Brian Benedict, Lake Worth, FL (US)

(73) Assignee: OHNOH2O, LLC, Lake Worth, FL (US)

( * ) Notice: Subject to any disclaimer, the term of this patent is extended or adjusted under 35 U.S.C. 154(b) by 0 days.

(21) Appl. No.: 17/502,931

(22) Filed: Oct. 15, 2021

(65) Prior Publication Data
US 2022/0120227 A1 Apr. 21, 2022

Related U.S. Application Data

(60) Provisional application No. 63/092,166, filed on Oct. 15, 2020.

(51) Int. Cl.
*F02D 41/00* (2006.01)
*F02D 19/06* (2006.01)

(52) U.S. Cl.
CPC ..... *F02D 41/0025* (2013.01); *F02D 19/0626* (2013.01); *F02D 2200/0611* (2013.01)

(58) Field of Classification Search
CPC ......... F02D 2200/0611; F02D 19/0626; F02D 41/0025
See application file for complete search history.

(56) References Cited

U.S. PATENT DOCUMENTS 4,539,108 A * 9/1985 Izutani ................ B01D 35/26
210/186
6,224,439 B1 5/2001 Sato et al.

FOREIGN PATENT DOCUMENTS

| EP | 1287252 | 3/2003 | |
|---|---|---|---|
| EP | 1287252 B1 * | 5/2006 | ........... B01D 36/005 |
| GB | 1392280 | 4/1975 | |

* cited by examiner

*Primary Examiner* — Kevin A Lathers
(74) *Attorney, Agent, or Firm* — McHale & Slavin, P.A.

(57) ABSTRACT

Systems, devices, and methods of using fuel quality indicators for indicating presence of water within a fuel source such as gasoline. The fuel quality indicator comprises a first indicating member and a second indicating member. The second indicating member is traversable to multiple positions relative to the first indicating member. The second indicating member is designed to float in the presence of water, sink in fuel such as gasoline, and be made of a material which maintains structural integrity when in the presence of fuels. In a preferred embodiment, the first indicating member and the second indicating member are co-axially aligned, with the second indicating member positioned over and oriented around the first indicating member.

15 Claims, 29 Drawing Sheets

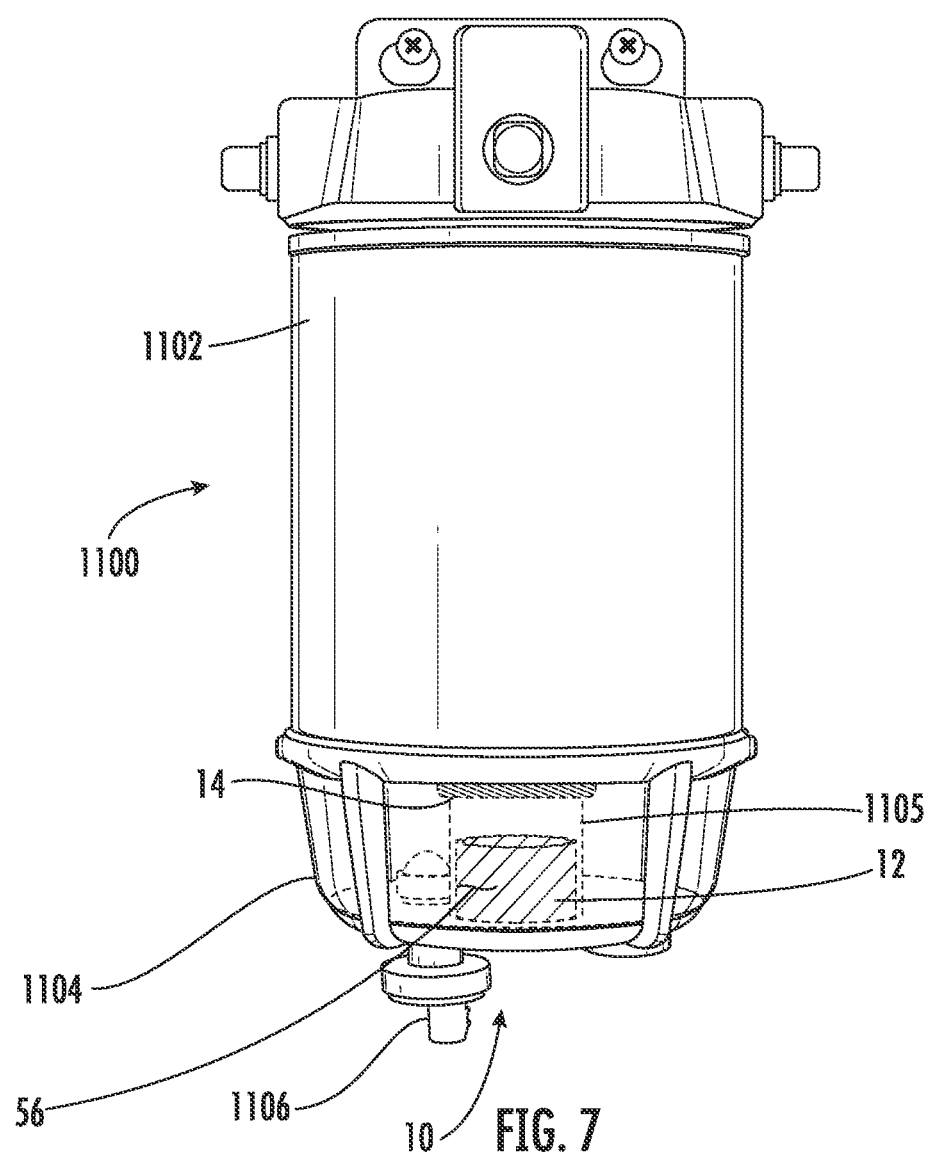

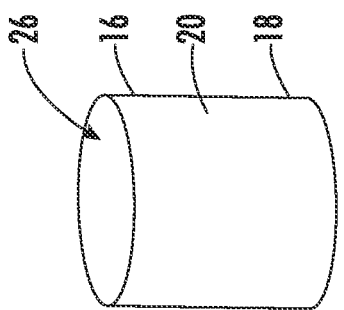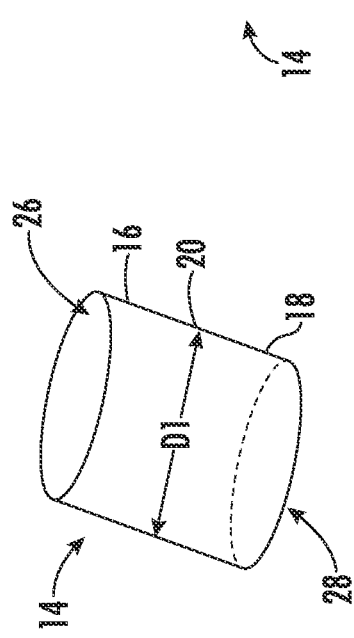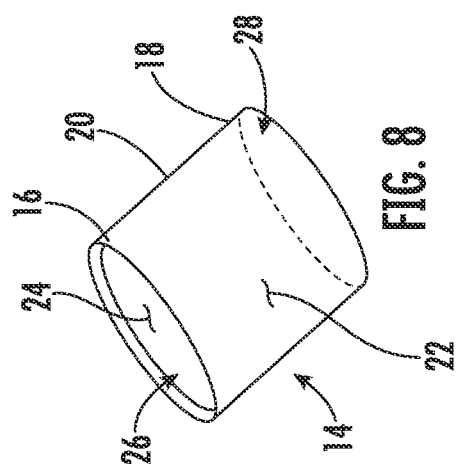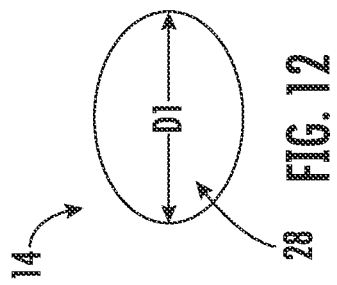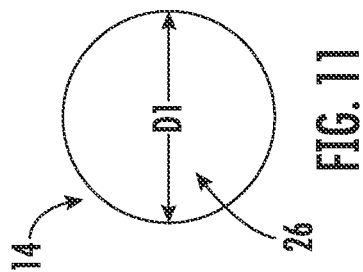

FUEL QUALITY INDICATOR

CROSS REFERENCE TO RELATED APPLICATION

In accordance with 37 C.F.R. 1.76, a claim of priority is included in an Application Data Sheet filed concurrently herewith. Accordingly, the present invention claims priority to U.S. Provisional Patent Application No. 63/092,166, entitled "FUEL QUALITY INDICATOR", filed on Oct. 15, 2020. The contents of the above referenced application are incorporated herein by reference in their entirety.

FIELD OF THE INVENTION

The invention is directed towards fuel indicators; to fuel quality indicators; and more particularly, to fuel quality indicators for indicating presence of water within a fuel source such as gasoline.

BACKGROUND OF THE INVENTION

Motor driven devices, such as boats, that use gasoline for powering the devices are well known in the art. Impurities and/or water mixed with gasoline can be problematic for these devices. Typically, water in boat engines can prevent the boat from operating smoothly, and, in many cases, from running at all. The risk of the engines failing to operate can result in a boat user being stuck in open waters, unable to safely navigate the marine vessel. This can result in a very dangerous situation, as the boat may only be capable of drifting through the water.

Because of the potential danger of water in the boat engine, most boat owners have developed systematic checks to prevent this from occurring. Typically, fuel water separators on the boat motor are visually checked to determine if water is accumulating in the fuel system. These fuel water separators often have a fluid collecting canister to aid the boat owner in determining if water has accumulated into the fuel system. Because water and gasoline do not mix and both have different densities, a boat user can see the separation between the two solutions when placed within the canister. While water is denser than gasoline and would form on the bottom-most layer of the canister, it can be difficult for a user to visualize the water-gasoline demarcation or separation line. While the fluid collecting canisters are transparent to allow the boat user easy viewing of the contents, over time the fluid collecting canisters become less transparent, making it much more difficult to the visualize the water-fuel separation line.

Therefore, what is needed in the art is an improved fuel quality indicator; particularly, a fuel quality indicator for indicating presence of water within a solution of gasoline in a quick and easily identifiable manner.

SUMMARY OF THE INVENTION

The invention is directed towards systems, devices, and methods of using fuel quality indicators. More particularly, the invention is directed towards systems, devices, and methods of using fuel quality indicators for indicating presence of water within a fuel source such as gasoline.

Accordingly, it is an objective of the invention to provide a fuel quality indicator system or device.

It is a further objective of the invention to provide a fuel quality indicator system or device for indicating presence of water within a solution of gasoline in a quick manner.

It is yet another objective of the invention to provide a fuel quality indicator system or device for indicating presence of water within a solution of gasoline in an easily identifiable manner.

It is a still further objective of the invention to provide a fuel quality indicator system or device for indicating presence of water within a solution of gasoline which uses multiple members having indicator surfaces.

It is a further objective of the invention to provide a fuel quality indicator system or device for indicating presence of water within a solution of gasoline which uses a second indicating member that is traversable to multiple positions relative to a first indicating member, depending on the amount of water.

Other objectives and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 7 illustrates the fuel quality indicator device as part of a fuel water separator with the fuel quality indicator device shown in the third position;

FIG. 8 is a perspective view of a second member of the fuel quality indicator device;

FIG. 9 is an alternative view of the second member of the fuel quality indicator device;

FIG. 10 is a front view of the second member of the fuel quality indicator device;

FIG. 11 is a top view of the second member of the fuel quality indicator device;

FIG. 12 is a bottom view of the second member of the fuel quality indicator device;

DETAILED DESCRIPTION OF THE INVENTION

Figure 1:
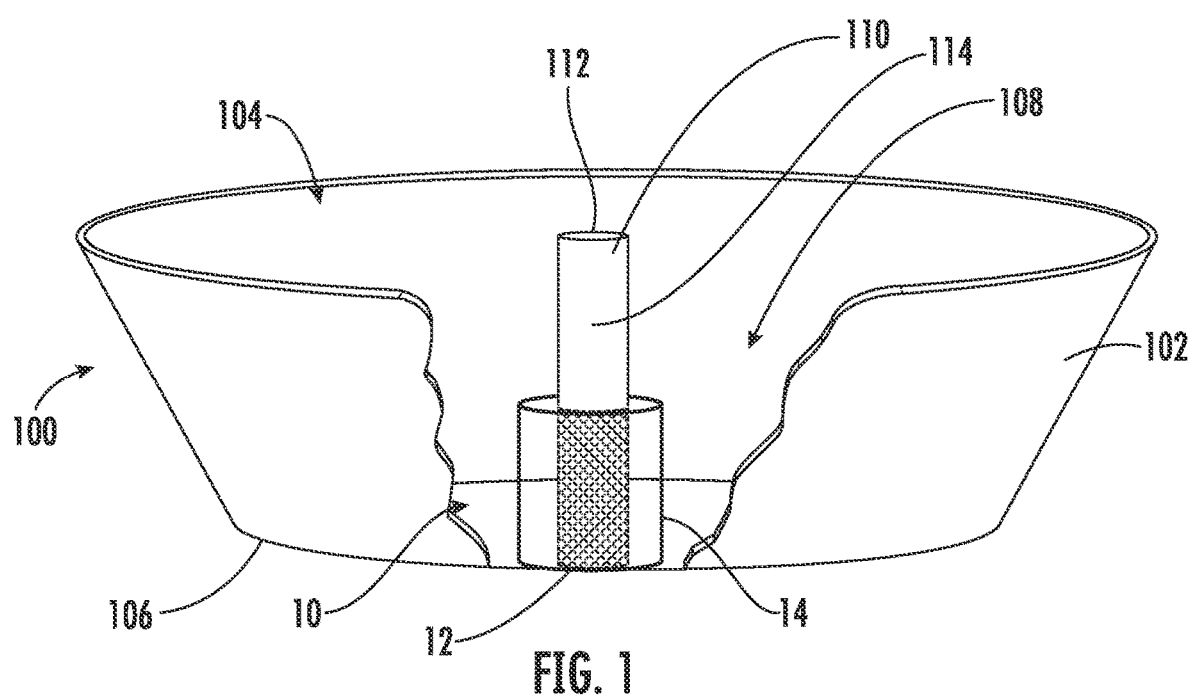
FIG. 1 shows an illustrative embodiment of a fuel quality indicator device shown in a first position.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

The present invention provides systems, devices, and methods of using fuel quality indicators for indicating presence of water within a fuel source such as gasoline. The systems, devices, and methods are designed to detect water levels within fuel source at the filter level, and not down at the motor level where it may be too late to effect change. FIG. 1 shows an illustrative embodiment of a fuel quality indicator device, referred to generally as fuel quality indicator 10. The fuel quality indicator 10 is described for use in indicating presence of water within a fuel source such as gasoline. However, such use is illustrative only, and where possible, the fuel quality indicator 10 may be used in other environments. As such, the fuel quality indicator 10 is shown placed within a fluid collecting canister 100. The fluid collecting canister 100 may be secured to a fuel water separator (not shown) and includes a continuous wall 102, an open top 104 and a closed bottom wall 106. Fluid may be inserted into and held within the interior 108.

The fluid collecting canister 100 may contain an elongated structure 110 extending upwardly from the bottom wall 106 towards the open top 104. The elongated structure 110 comprises an open end 112 with an interior 114. The elongated structure interior 114 may be hollow or partially hollow to receive and hold an object. The elongated structure interior 114 may be cylindrical in shape. The fluid collecting canister 100 may be a pre-existing unit, such as those made by RACOR. In such a case, the fuel quality indicator 10 may be configured to retrofit a pre-existing fluid collecting canister 100.

Figure 5:
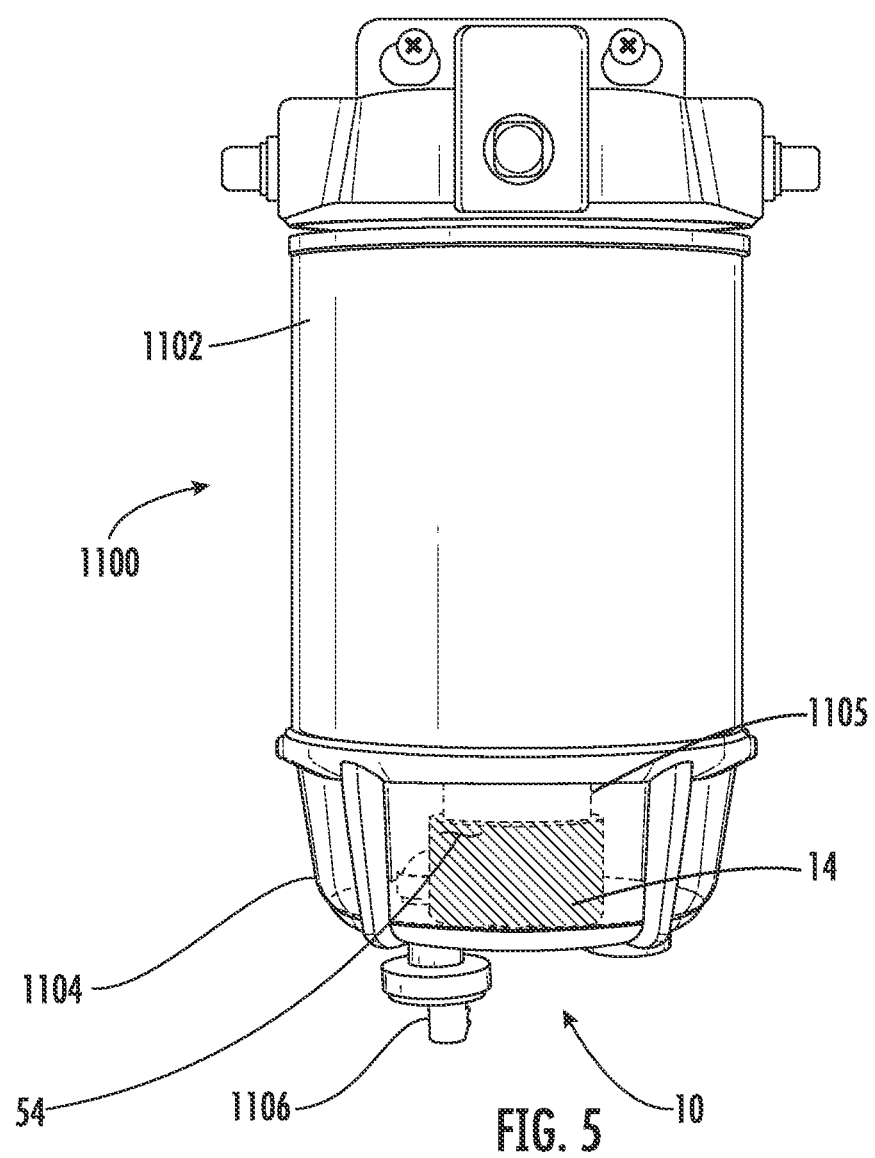
FIG. 5 illustrates the fuel quality indicator device as part of a fuel water separator with the fuel quality indicator device shown in the first position.
Figure 6:
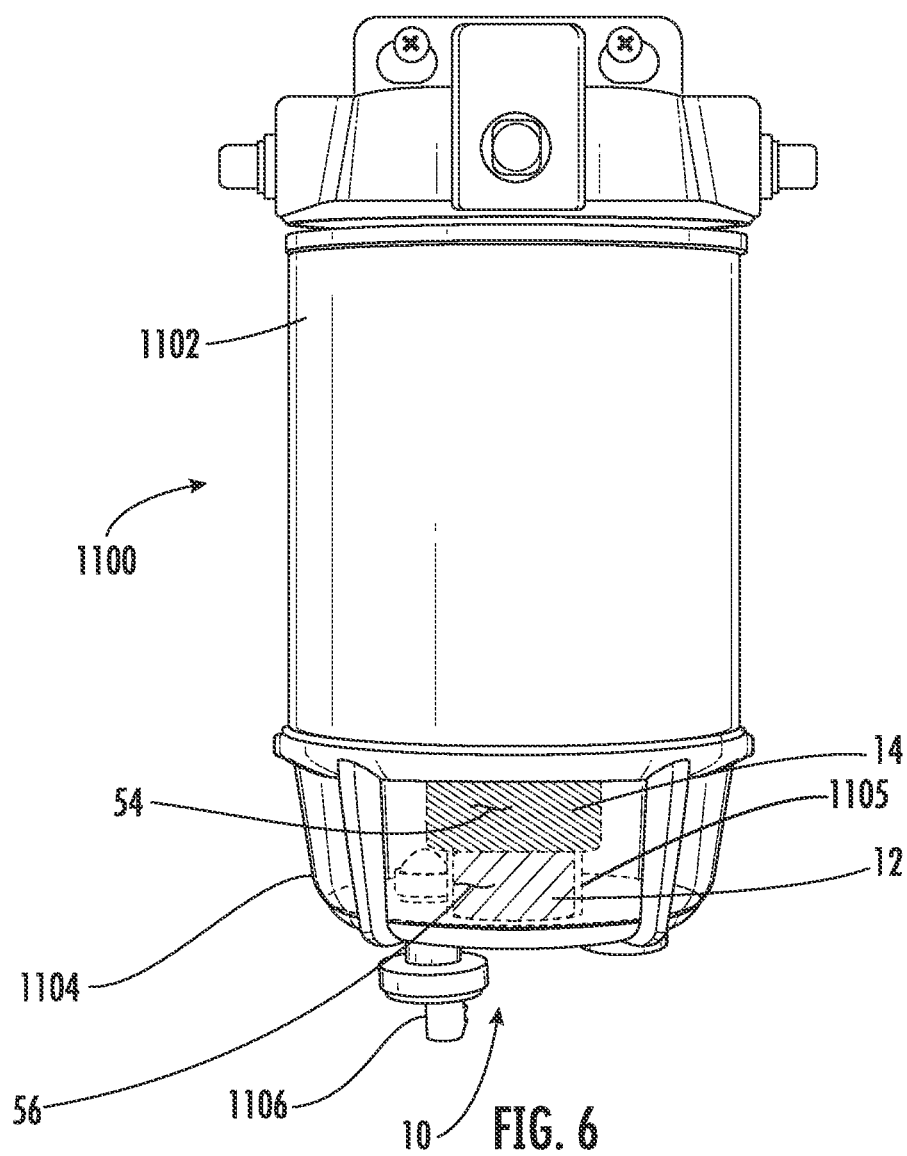
FIG. 6 illustrates the fuel quality indicator device as part of a fuel water separator with the fuel quality indicator device shown in the second position.
Figure 13:
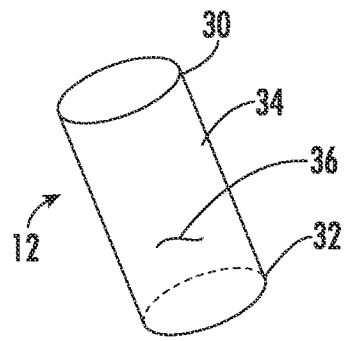
FIG. 13 is a perspective view of a first member of the fuel quality indicator device.
Figure 14:
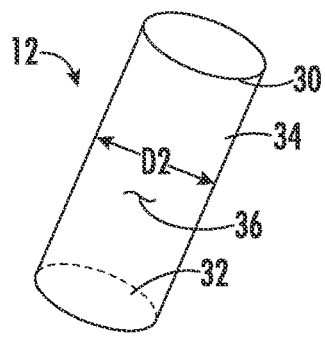
FIG. 14 is an alternative view of the first member of the fuel quality indicator device.
Figure 15:
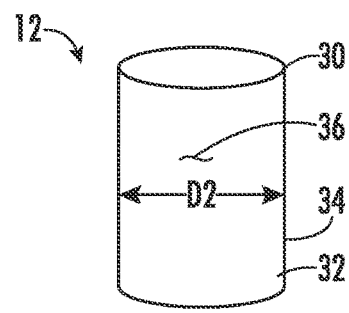
FIG. 15 is a front view of the first member of the fuel quality indicator device.
Figure 16:
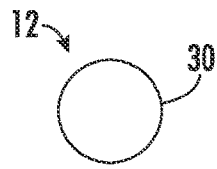
FIG. 16 is a top view of the first member of the fuel quality indicator device.
Figure 17:
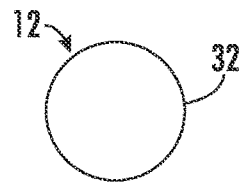
FIG. 17 is a bottom view of the first member of the fuel quality indicator device.

Alternatively, the fuel quality indicator 10 may be part of a fuel water separator 1100 (may also be referred to as a fuel filter/water separator), see FIGS. 5-7. The fuel water separator 1100 comprises an outer casing 1102 which holds a filter unit (not shown) and a fluid container 1104 having fluid outlet 1106. As illustrated in the figures, the fuel quality indicator 10 is part of the fluid container 1104, preferably fitting on or over an elongated structure or shaft 1105, which acts as a fuel quality indicator support structure. The elongated structure or shaft 1105 is shown as a cylindrical body positioned within the center of the fluid container 1104.

The fuel quality indicator 10 comprises a first indicating member 12 and a second indicating member 14. The second indicating member 14 is designed to float in the presence of water, sink in fuel, such as gasoline, and be made to maintain structural integrity when in the presence of fuels such as gasoline. Preferably, the second indicator 14 is made from High Density Polyethylene (HDPE) having a high chemical resistance to gasoline, and having specific gravity of less than 1.0, such as between 0.75 and less than 1.0, and preferably in the range of 0.9 or 0.95. The HDPE material may also be UV stable. In a preferred embodiment, the first indicating member 12 and the second indicating member 14 are co-axially aligned, with the second indicating member 14 positioned over and oriented around the first indicating member 12, see FIG. 1. Preferably the first indicating member 12 is sized and shaped be inserted into and fit within the interior 114 of the elongated structure 110. The second indicating member 14 is arranged to move in an upward or downward direction relative to the first indicating member 12, which is preferably fixed in position, but not required to be.

Referring to FIGS. 8-12, the second indicating member 14 is shown independent of the first indicating member 12. The second indicating member 14 comprises a first end 16, an opposing second end 18, and a main body 20. The main body 20 is shown as a continuous wall having a generally cylindrical shape. Such shape, however, is illustrative only and other shapes may be used. The main body 20 has an outer surface 22 and an inner surface 24. To allow the first indicating member 12 and the second indicating member 14 to be aligned in a co-axial position, the second indicating member first end 16 has an opening 26 and the second indicating member second end 18 has an opening 28.

Figure 18:
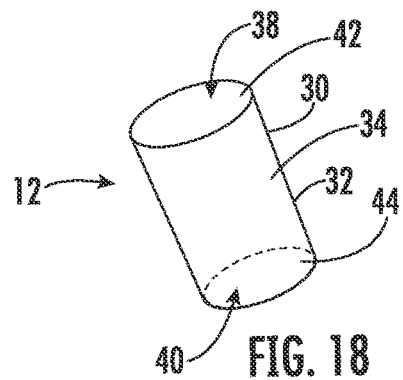
FIG. 18 is a perspective view of the first member of the fuel quality indicator device, shown with opposing open ends.

Referring to FIGS. 13-17, the first indicating member 12 is shown independent of the second indicating member 14. The first member 12 comprises a first end 30, an opposing second end 32, and a main body 34. The first member main body 34 is shown as a continuous wall having a generally cylindrical shape. Such shape, however, is illustrative only and other shapes may be used. The first indicating member main body 34 has an outer surface 36. The first indicating member first end 30 and the first indicating member second end 32 may be closed or solid ends. Alternatively, the first indicating member first end 30 may have an opening 38 and the first indicating member second end 32 may have an opening 40, with the interior 42 forming an inner surface 44, see FIG. 18. The interior 42 may be hollow or partially hollow.

To allow for a coaxial relationship, or for the second indicating member 14 to move relative to the first indicating member 12, the second indicating member main body 20, the second indicating member first end opening 26 or the second member second end opening 28 preferably have a diameter D1 that is larger than the diameter D2 of the first indicating member 12.

Figure 19A:
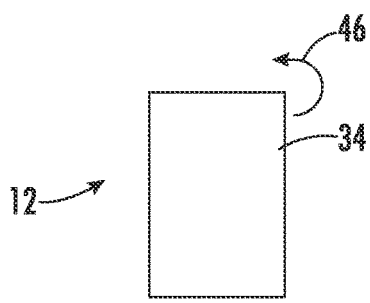
FIG. 19A is an alternative embodiment of the first member of the fuel quality indicator device, shown as a bendable sheet.
Figure 19B:
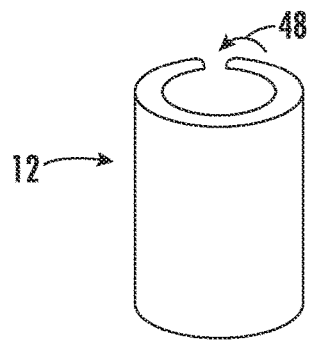
FIG. 19B illustrates the bendable first member of the fuel quality indicator sheet, in a bended and rolled orientation.

While the first indicating member 12 may be designed to be inserted into and fit within the interior 114 of the elongated structure 110, as shown in FIG. 1 or FIG. 5, FIGS. 19A and 19B illustrate an alternative embodiment of the first indicating member 12 of the fuel quality indicator 10. In the embodiment illustrated, the first indicating member main body 34 is a bendable or foldable sheet. The bendable or foldable sheet may be bent or folded, see arrows 46 and 48, thereby to arrange the sheet of the main body 34 into a particular shape, i.e. form a planar sheet shape (FIG. 19A) into a cylindrical shape (FIG. 19B).

In use, the fuel quality indicator 10 is designed to provide an easy to use and understand mechanism to indicate visually that gasoline does or does not contain water. In the presence of water, the second indicating member 14 is designed to float and move relative to the first indicating member 12. Referring back to FIGS. 1-3, the fuel quality indicator 10 is shown inside the canister 100, with a portion of the wall 102 cut out for visualization. The canister 100 is shown without any fluid for illustration purposes. FIG. 1 shows an illustrative embodiment of the fuel quality indicator 10 in a first position. In this position, the second indicating member 14 is completely covering the first indicating member 12 so that a user is unable to see the first indicating member 12.

Figure 2:
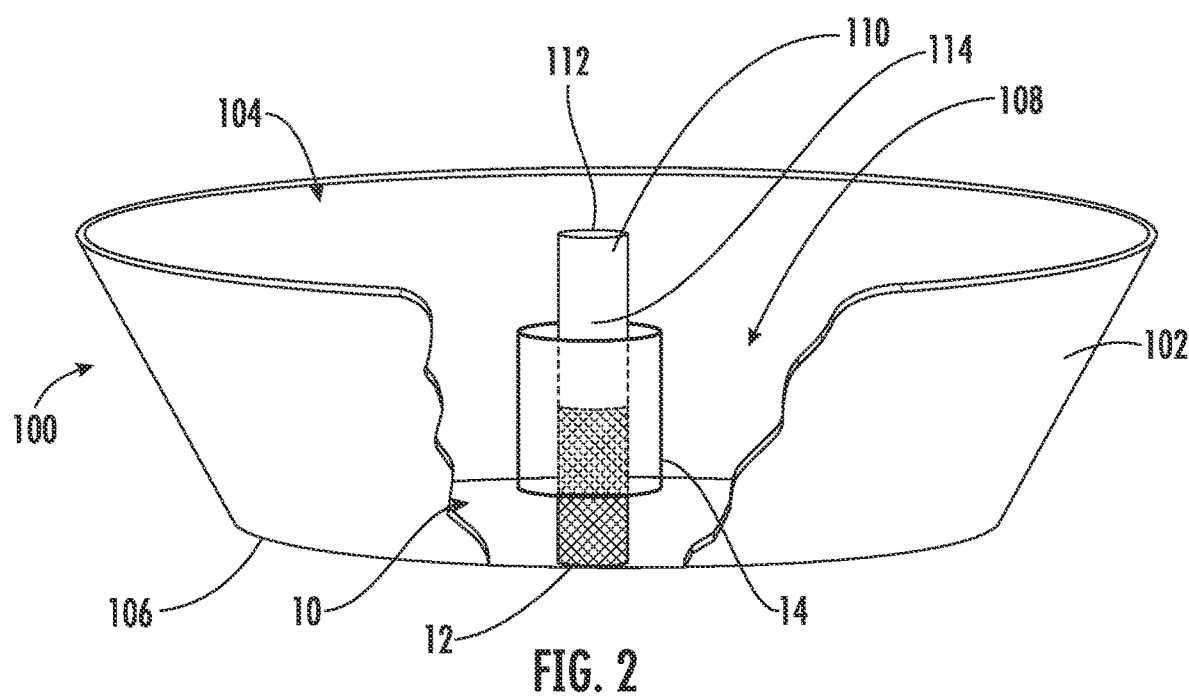
FIG. 2 shows an illustrative embodiment of the fuel quality indicator device shown traversed to a second position.
Figure 3:
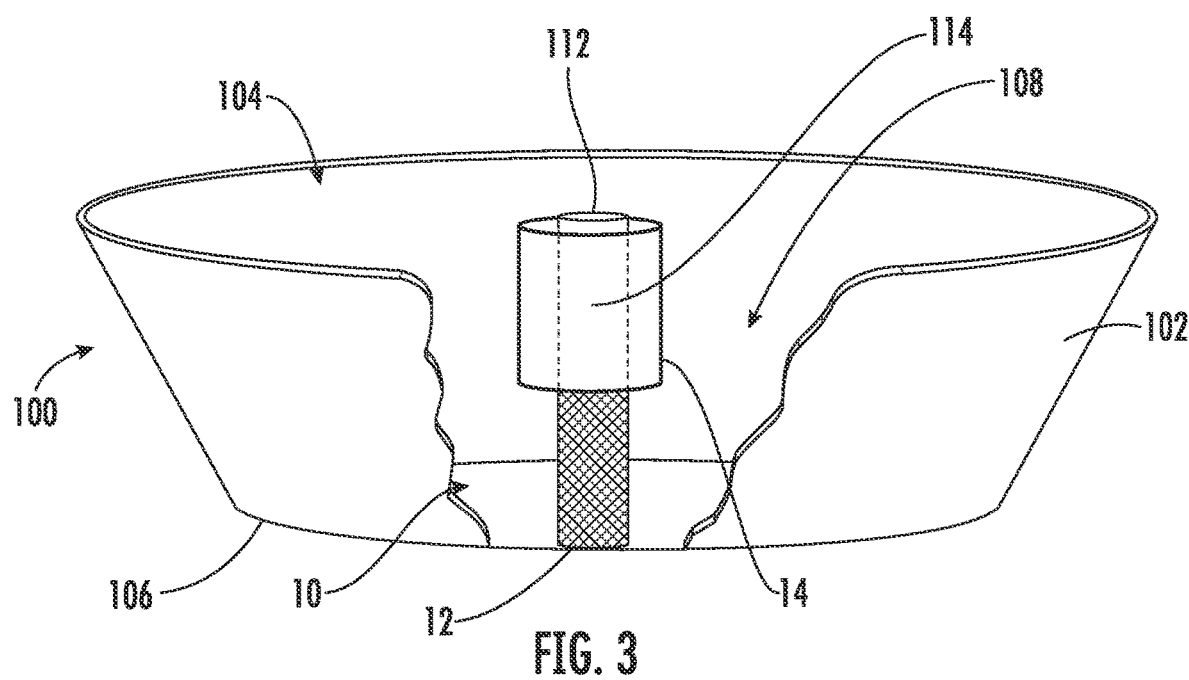
FIG. 3 shows an illustrative embodiment of the fuel quality indicator device shown traversed to a third position.
Figure 4:
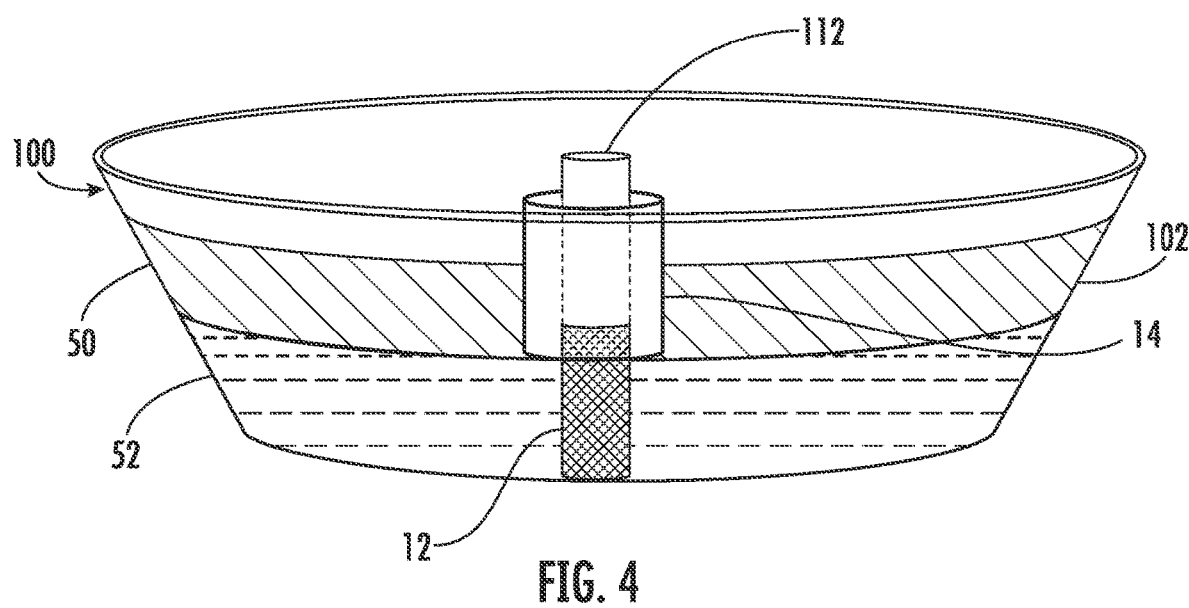
FIG. 4 illustrates the fuel quality indicator device within a water/gasoline solution.

FIG. 2 shows an illustrative embodiment of the fuel quality indicator 10 traversed to a second position. In this position, the second indicating member 14 is moved upwardly relative to the first indicating member 12 so that a user is unable to see at least a portion of the first indicating member 12. FIG. 3 shows the fuel quality indicator 10 traversed to a third position. In this position, the second indicating member 14 is moved completely past or nearly past the first indicating member 12 so that a user is able to see most, if not all, of the first indicating member 12. FIG. 4 shows the container 100 with gasoline 50 and water 52. The fuel quality indicator 10 is shown in the third position. In this position, the fuel quality indicator 10 floats as a result of the presence of water.

Preferably, the first indicating member 12 and the second indicating member 14 contain indicators. Such indicators are preferably colors, but may be words or letters. As illustrated in FIG. 5, the second indicating member 14 is shown having an indicator with a green color surface 54 (may be referred to as a second visual indicator). FIG. 6 illustrates the first indicating member 12 having an indicator with a red surface 56 (may be referred to as a first visual indicator). In this configuration, a user can easily determine if the gasoline in the fluid container 1104 contains water by looking at the indicator surfaces 54 or 56. In the illustration in FIG. 5, a user only sees the green color surface 54, indicating there is no water present. In FIG. 6, the user can see both the second indicating member green color surface 54 and the first indicating member red color surface 56, indicating the presence of some water within the gasoline. The higher the second indicating member green color surface 54 floats up, exposing more of the first indicating member red color surface 56, the greater the amount of water. FIG. 7 shows predominately, if not only, the first indicating member red color surface 56. This indicates a large presence of water within the fuel.

Figure 20A:
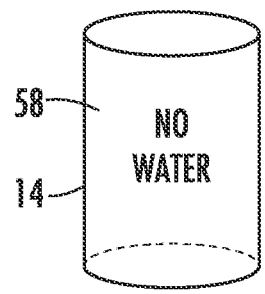
FIG. 20A illustrates the second member of the fuel quality indicator device having word based indicators.
Figure 20B:
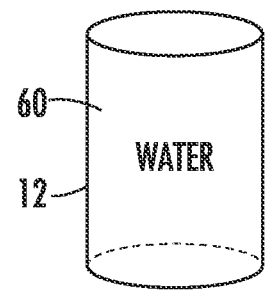
FIG. 20B illustrates the first member of the fuel quality indicator device having word based indicators.
Figure 20C:
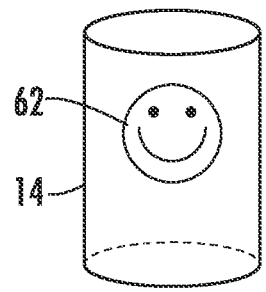
FIG. 20C illustrates the second member of the fuel quality indicator device having picture based indicators.
Figure 20D:
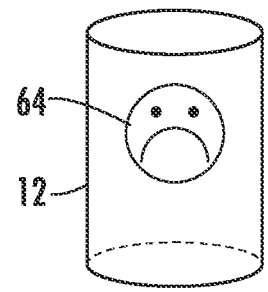
FIG. 20D illustrates the first member of the fuel quality indicator device having picture based indicators.

While the first indicating member 12 and the second indicating member 14 are described as having colored surface based indicators, other indictors may be used. The first indicating member 12 and the second indicating member 14 may use words, letters, symbols, pictures, or other types of indicia. FIG. 20A shows an illustrative example of the second indicating member 14 using a word-based indicator 58, illustrated as "NO WATER", to indicate no water within the fuel. FIG. 20B shows an illustrative example of the first indicating member 12 using a word-based indicator 60, illustrated as "WATER", to indicate the presence of water within the fuel. FIG. 20C shows an illustrative example of the second indicating member 14 using a symbol or picture based indicator 62, illustrated as a picture of a smile or happy face, to indicate no water within the fuel. FIG. 20D shows an illustrative example of the first indicating member 12 using a symbol or picture based indicator 64, illustrated as a picture of an unhappy or frown face, to indicate the presence of water within the fuel.

Figure 21:
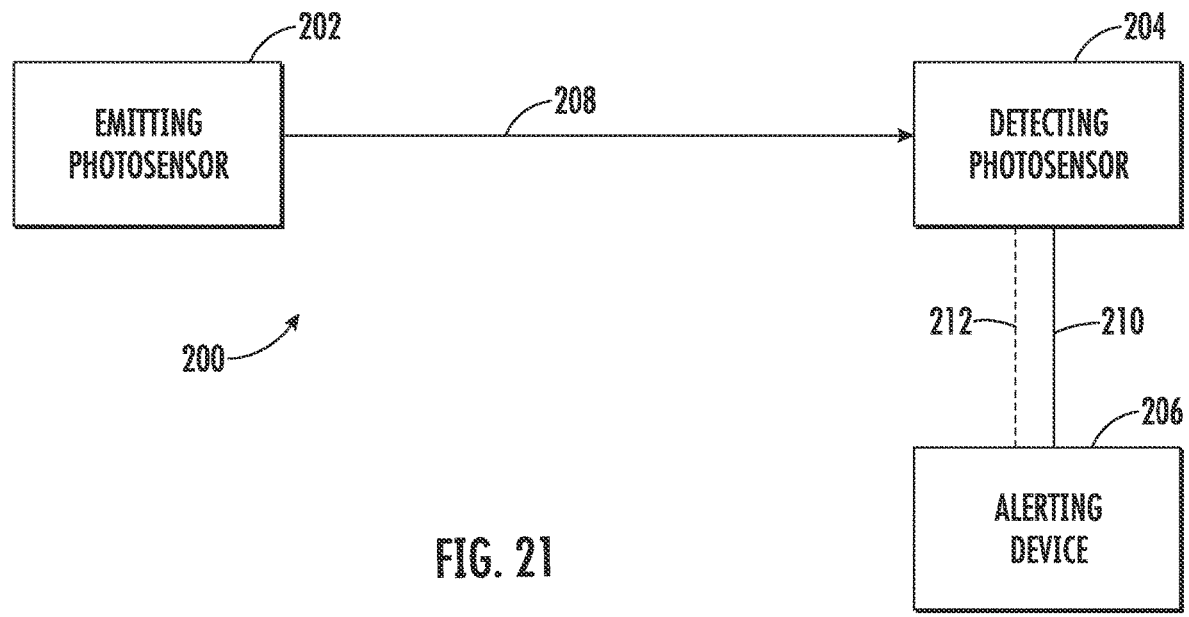
FIG. 21 illustrates a schematic representation of a fuel quality indicator device remote alert system.

FIG. 21 illustrates a schematic representation of a fuel quality indicator device remote alert system; referred to generally as a remote alert system 200. The remote alert system 200 is designed as an additional alert mechanism to indicate the presence of water within the fuel. The remote alert system 200 may comprise a first sensor 202, preferably a photo emitting/sending sensor, a second sensor 204, preferably a photo detecting/receiving sensor, and an indicator or alerting device 206. The first sensor 202 and the second sensor 204 are preferably spaced apart (such as separated 180 degrees apart) and aligned so that the second sensor 204 detects or receives an electromagnetic radiation signal 208, such as a laser or LED beam generated from the first sensor 202. The second sensor 204 is operatively connected to the indicator or alerting device 206 via wires 210 or wirelessly 212 via, for example, WIFI or BLUETOOTH. The indicator or alerting device 206 is configured to provide an alert via, for example, production of sound, lights, or other mechanisms known to one of skill in the art.

Figure 22:
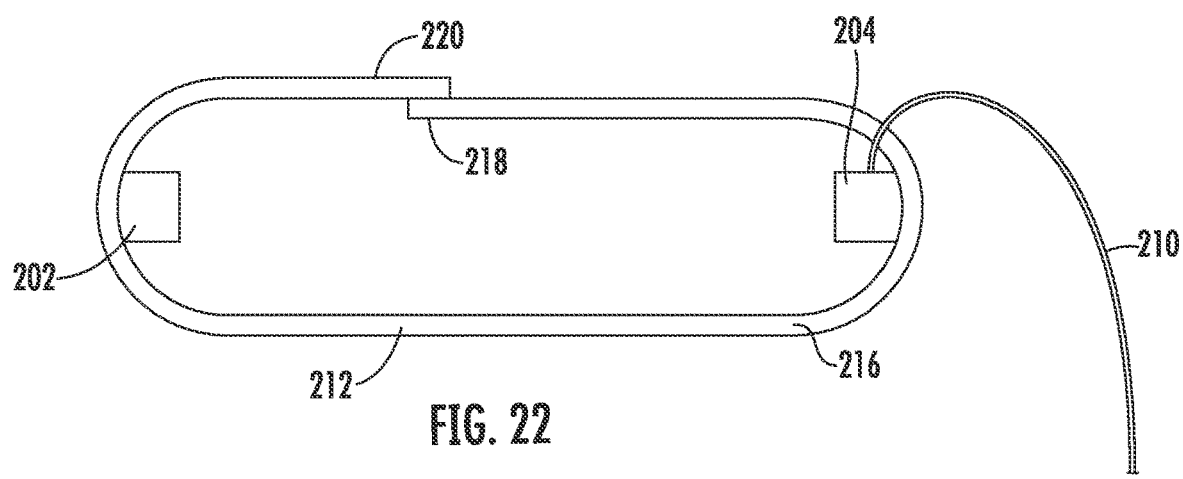
FIG. 22 is an illustrative embodiment of a fuel quality indicator device remote alert attachment member.

FIG. 22 is an illustrative embodiment of a fuel quality indicator device remote alert attachment member 212. The fuel quality indicator device remote alert attachment member 212 comprises a main body 216 having a first end 218 securable to a second end 220 via a securing mechanism known to one of skill in the art, such as via buttons, chemical fastening such as glue, hook and loop fastening such as VELCRO, and buckles. The main body 216 may be constructed of a stretchable material, such as a plastic material. The first sensor 202 and the second sensor 204 may be secured to the main body 216 and aligned so that the second sensor 204 detects or receives an electromagnetic radiation signal 208, such as a laser or LED beam generated from the first sensor 202.

Figure 23:
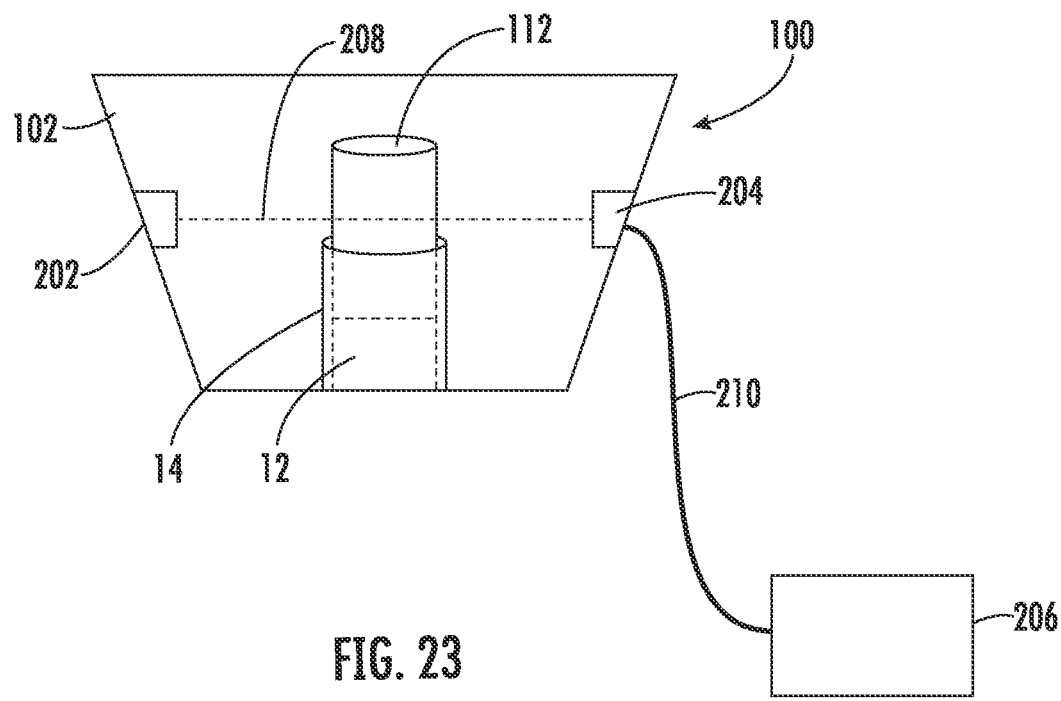
FIG. 23 illustrates the fuel quality indicator device remote alert system attached to a canister of the fuel water separator.
Figure 24:
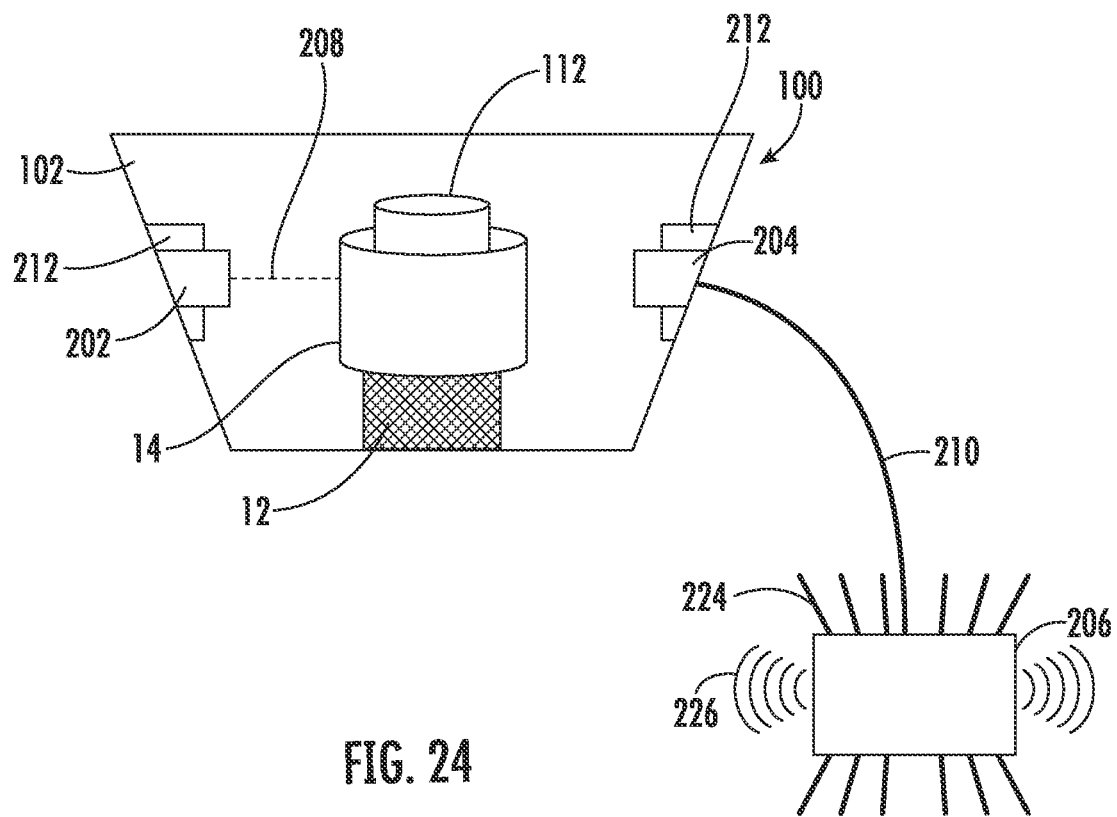
FIG. 24 illustrates the fuel quality indicator device remote alert system attached to a canister of the fuel water separator, shown with an alarm indicator being tripped.

FIG. 23 illustrates the fuel quality indicator device remote alert attachment member 212 attached to the wall 102 of the fluid collecting canister 100. In this figure, the first sensor 202 and the second sensor 204 are positioned so that the laser 208 rests just above the second indicating member 14. In the presence of water, the second indicating member 14 moves upwardly, into the pathway of the laser 208. This movement causes a break in the laser photo pathway to the second sensor 204, causing the wire 210 to send a signal to and trip or activate the indicator or alerting device 206, see FIG. 24. Once tripped or activated the indicator or alerting device 206 produces a light energy 224, sound energy 226, or combinations thereof. The light energy may be white light or any colored light, pulsing light, flashing light, or a change in color from green to red. The sound energy 226 may be a continuous sound or pitch, pulses, or a voice based message. The light energy 224 or sound energy 226 thus being used to alert a user of the presence of water in the fluid. The indicator or alerting device 206 may be configured to send a text message to a cell phone or email message to a computer.

Figure 25:
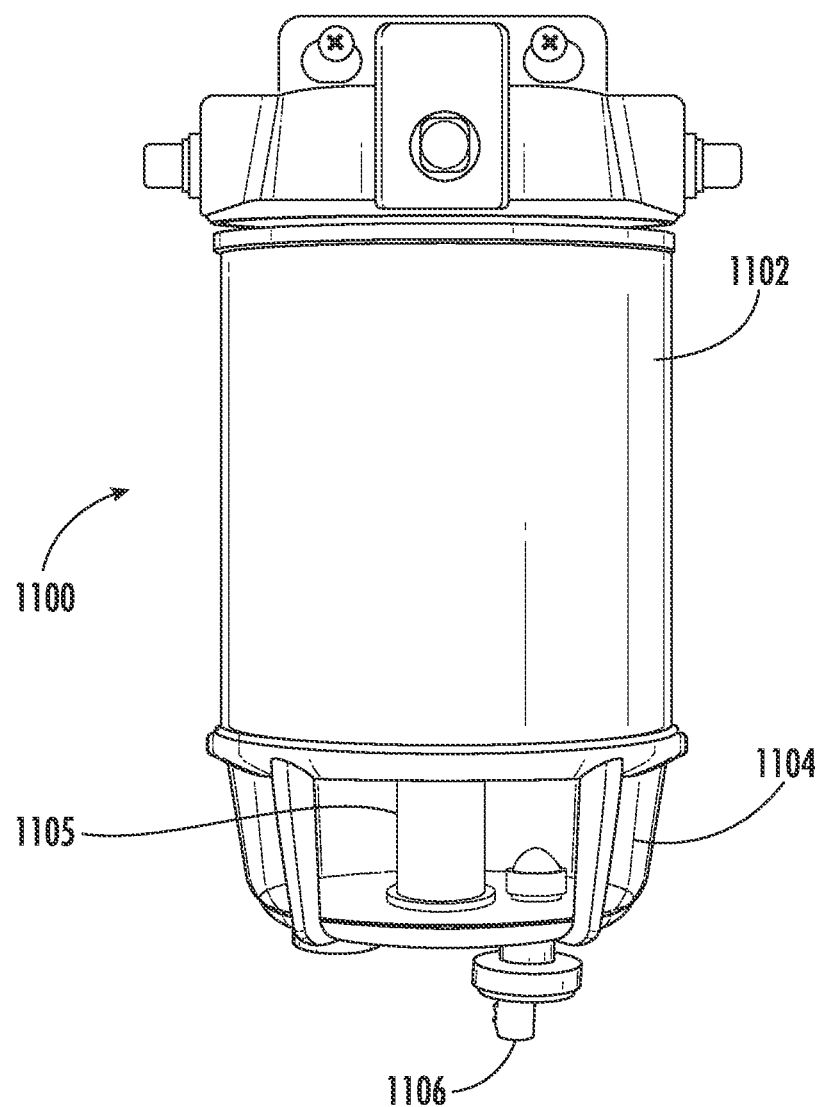
FIG. 25 illustrates a fuel filter shown without the fuel quality indicator device.
Figure 26:
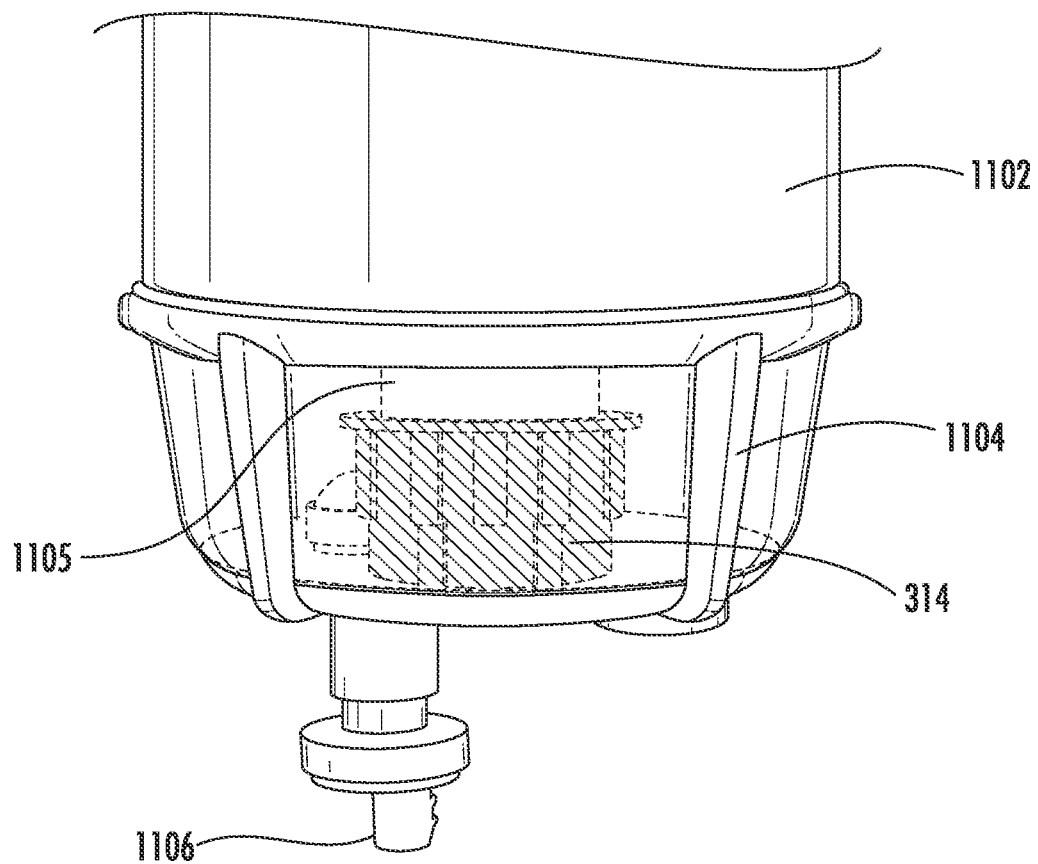
FIG. 26 illustrates a fuel filter water separator shown with an alternative embodiment of the fuel quality indicator device, with the second indicating member positioned over the first indicating member, indicating "sinking" in the presence of fuel.
Figure 27:
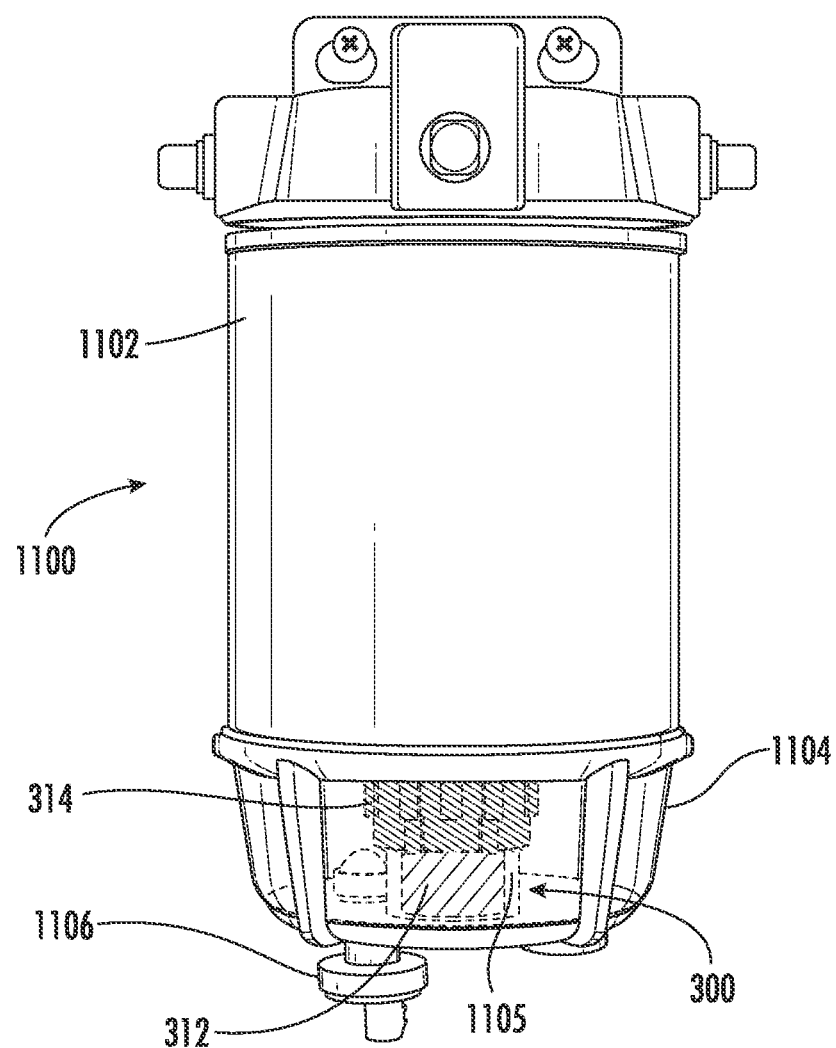
FIG. 27 illustrates a fuel filter water separator shown with an alternative embodiment of the fuel quality indicator device, with the second indicating member positioned above the first indicating member, indicating "floating" in the presence of water.
Figure 28:
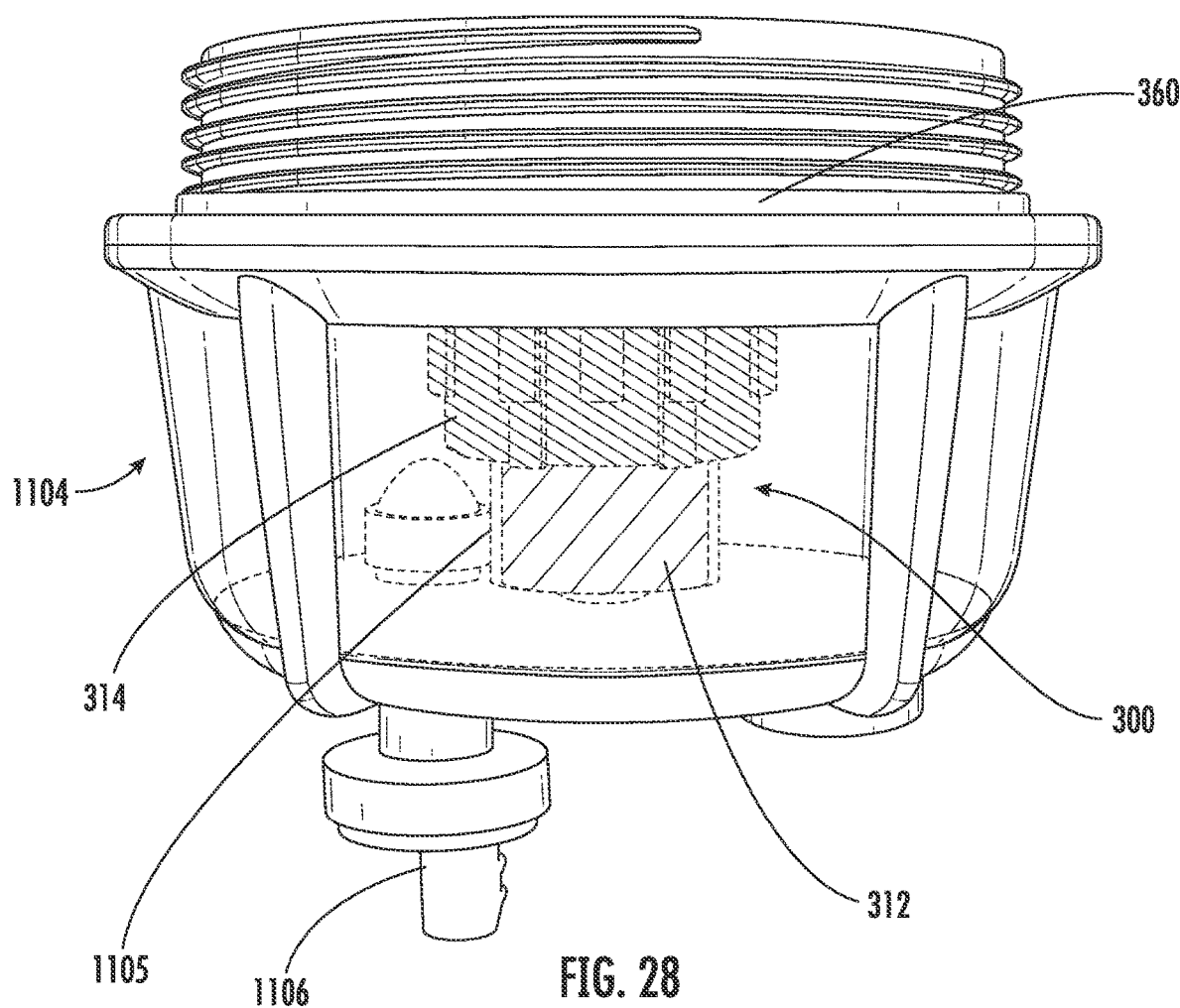
FIG. 28 illustrates the fuel filter water separator bowl separated from the fuel filter water separator body.

Referring to FIGS. 25-27, the fuel water separator 1100 is shown with an alternative embodiment of the fuel quality indicator, referred to generally as fuel quality indicator 300. The fuel indicator 300 functions in the same manner as that described for fuel quality indicator 10. The fuel indicator 300 may comprise a first indicating member 312 and a second indicating member 314. Except where indicated, the first indicating member 312 may include any of the features or structures described for or associated with the first indicating member 12. Except where indicated, the second indicating member 314 may include any of the features or structures described for or associated with the second indicating member 14. The second indicating member 314 is designed to float in the presence of water, sink in fuel such as gasoline, and be made to maintain structural integrity when in the presence of fuels such as gasoline. Referring to FIG. 25, the fuel water separator 1100 is shown without the fuel indicator 300 positioned or placed over a fuel quality indicator support structure, illustrated as the elongated structure or shaft 1105. The fuel quality indicator support structure 1105 should be sized and shaped to allow the first indicator member 312 (or 12) to fit within, 2) allow the second indicator member 314 (or 14) to fit over and vertically, move up or down, and 3) maintain the second indicator member 314 in position, i.e. not float or move horizontally, left or right (or not move in a direction other than vertically), from its position while in the presence of a fluid.

FIG. 26 illustrates the fuel indicator 300 positioned or placed over elongated structure or shaft 1105, with the second indicating member 314 positioned over the first indicating member 312 (the first indicating member 312 placed within the interior of the elongated structure or shaft 1105), indicating "sinking" in the presence of fuel. FIG. 27 illustrates the second indicating member 314 positioned above the first indicating member 312, indicating "floating" in the presence of water.

Figure 30:
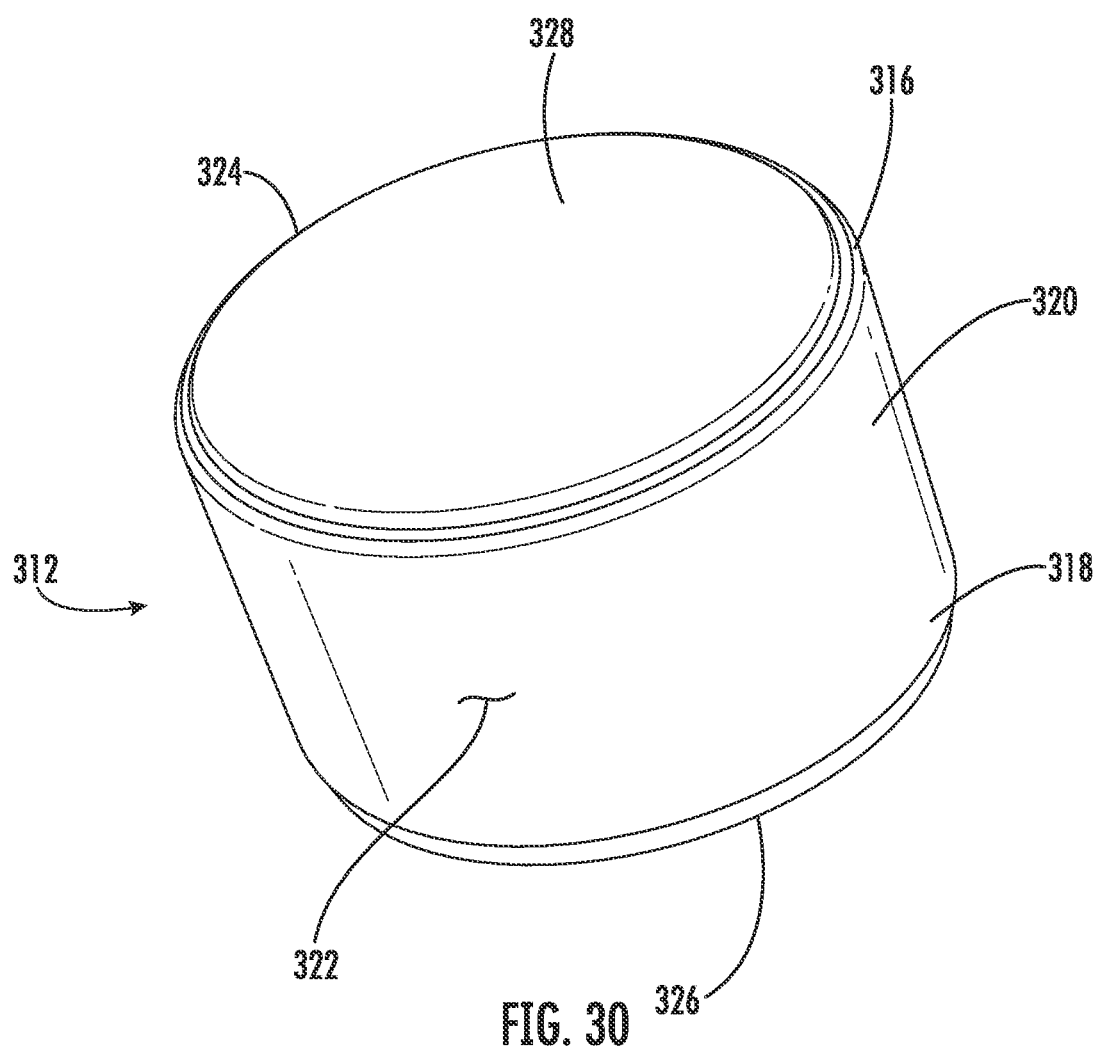
FIG. 30 is a perspective view of an illustrative embodiment of the first indicating member of the fuel quality indicator device illustrated in FIG. 27.

Referring to FIG. 30, an embodiment of the first indicating member 312 is shown. The first indicating member 312 comprises a first end 316, an opposing second end 318, and a main body 320. The first member main body 320 is shown as a continuous wall having a generally cylindrical shape. Such shape, however, is illustrative only and other shapes may be used. The first indicating member main body 320 has an outer surface 322. The first indicating member first end 316 or the first indicating member second end 318 may be closed or have solid ends. Alternatively, the first indicating member first end 316 may have an opening 324 and the first indicating member second end 318 may have an opening 326, with the interior 328 forming an inner surface. The interior may be hollow or partially hollow. The first indicating member first end 316 and second end 318) may optionally include a cap 328. The cap 328 may help the user visualize the colors when a user is viewing at certain angles.

To allow for a coaxial relationship or for the second indicating member 314 to move relative to the first indicating member 312, the diameter of the first indicating member 312 is smaller than the diameter of the second indicating member 314. In addition, the diameter of the first indicating member 312 is larger than the diameter of the fluid container elongated structure 1105.

Figure 31:
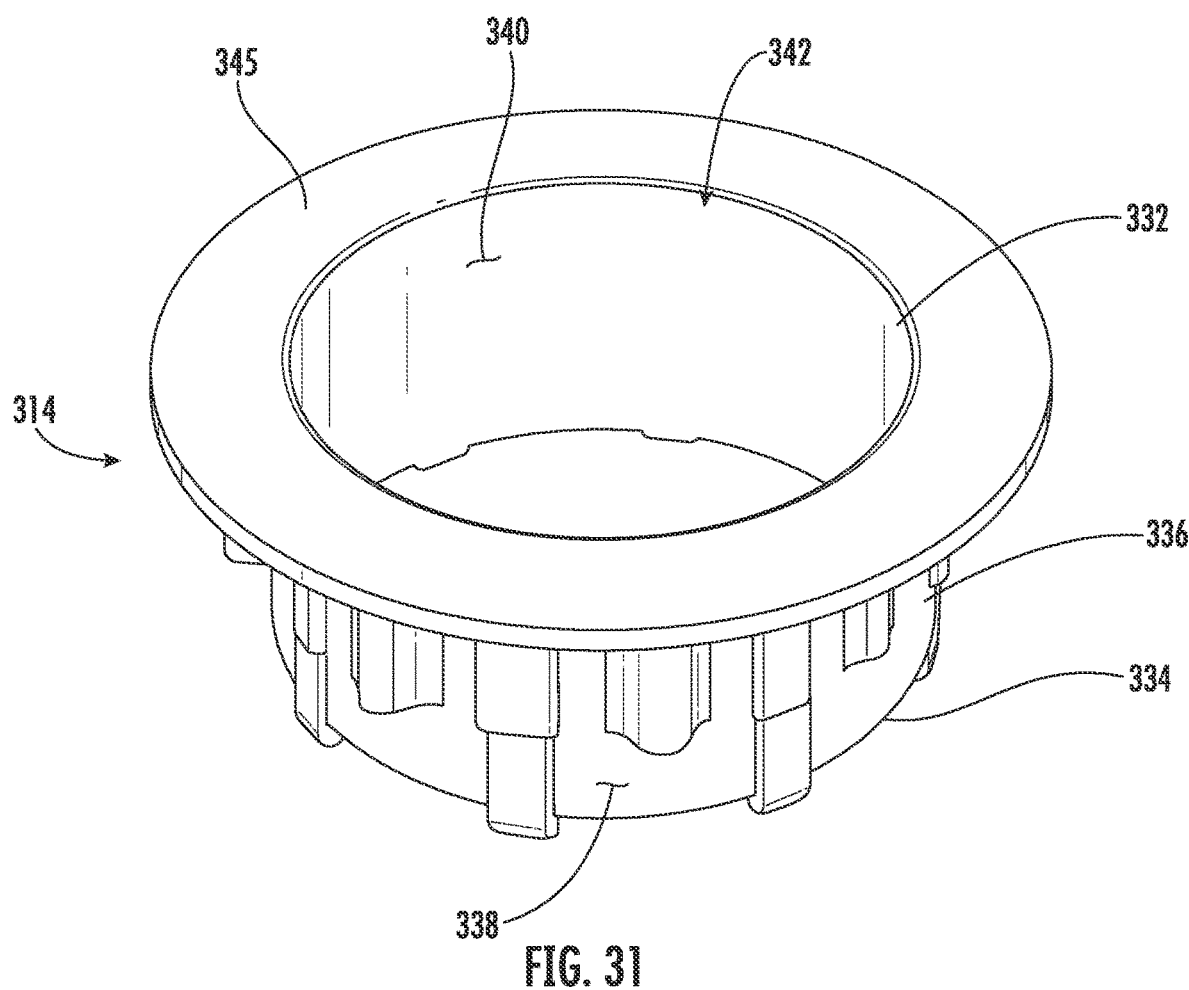
FIG. 31 is a top perspective view of an illustrative embodiment of the second indicating member of the fuel quality indicator device illustrated in FIG. 26.
Figure 32:
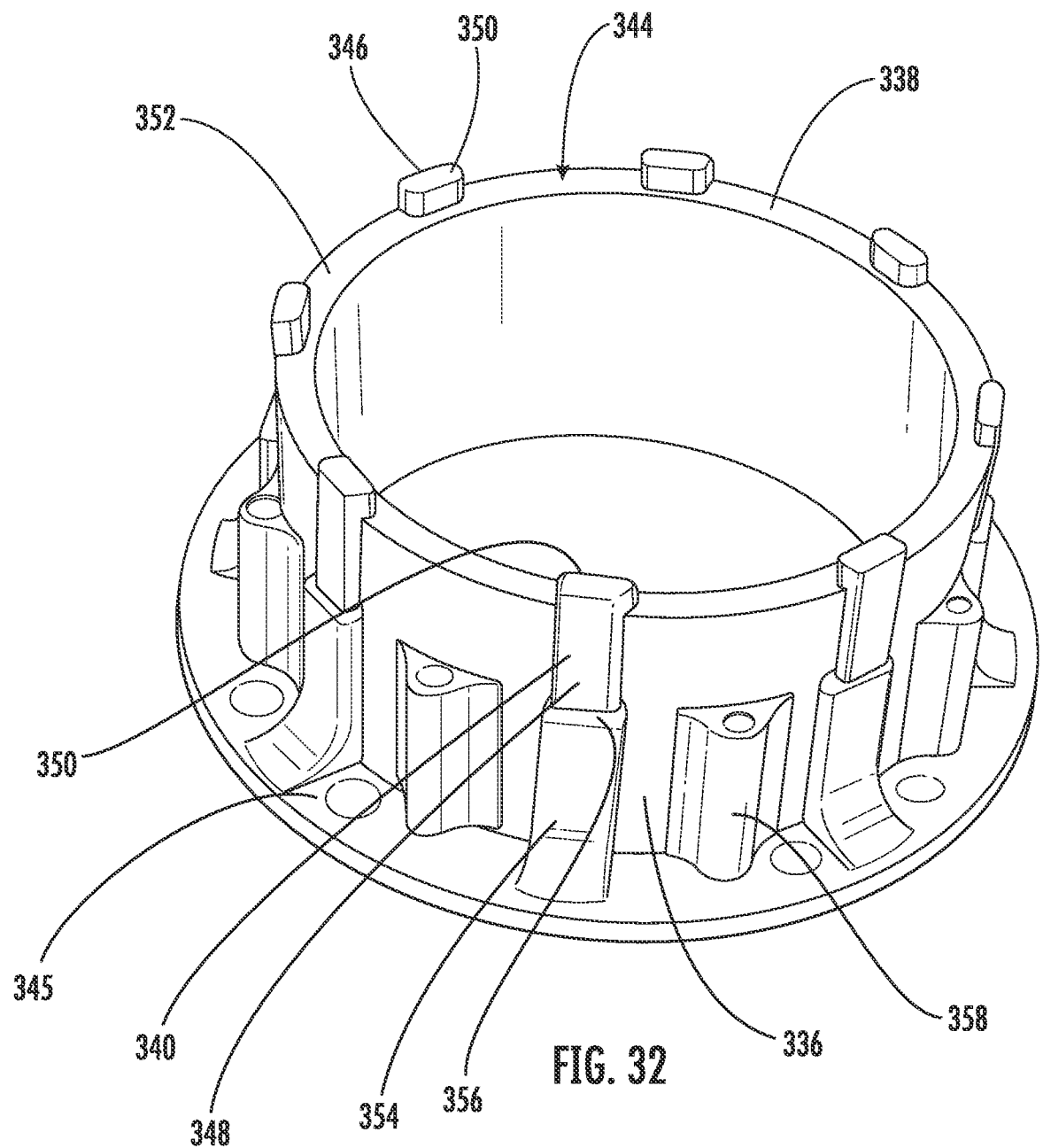
FIG. 32 is a bottom perspective view of the second indicating member of the fuel quality indicator device illustrated in FIG. 31.
Figure 33:
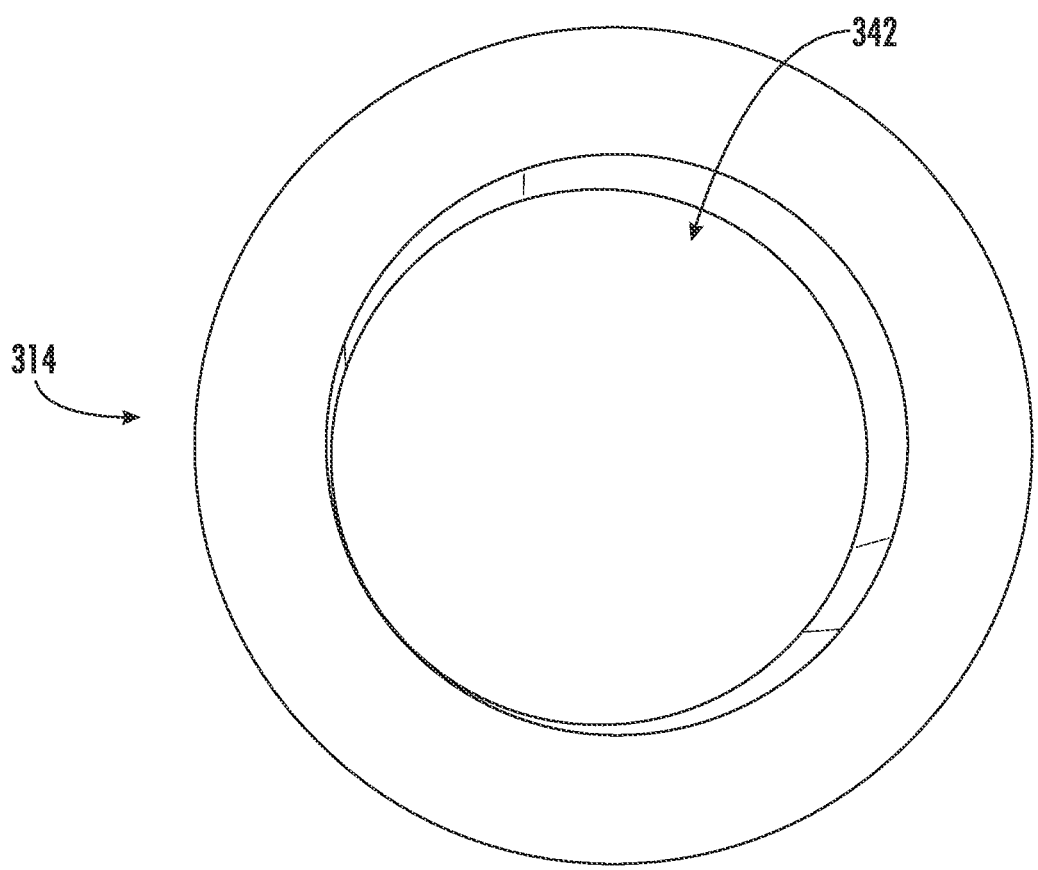
FIG. 33 is a top view of the second indicating member of the fuel quality indicator device illustrated in FIG. 31.

Referring to FIGS. 31-33, an embodiment of the second indicating member 314 is shown. The second indicating member 314 comprises a first end 332, an opposing second end 334, and a main body 336. The main body 336 is shown as a continuous wall having a generally cylindrical shape. Such shape, however, is illustrative only and other shapes may be used. The main body 336 has an outer surface 338 and an inner surface 340. To allow the first indicating member 312 and the second indicating member 314 to be aligned in a co-axial position, the second indicating member first end 332 has an opening 342 and the second indicating member second end 338 has an opening 344. The first opening 342 and the second opening 344, along with the main body 336 is sized and shaped to fit over the fluid container elongated structure 1105 (or fluid collecting canister elongated structure or shaft 110 for second indicator 14). The main body 336 may also contain a flange or surface 345 at, and encircling, the first end 332. The flange or surface 345 extends out and away from the main body 336.

The second indicating member main body 336 may contain one or more surface body members. For example, the second indicating member main body 336 may contain one or more feet members 346. The feet member 346 may contain a body 348 having a terminal end 350 that extends out, or away from the surface 352 of the second indicating member second end 334. A portion of the body may be, but not necessarily, designed to extend partially within the second indicating member main body 336. The second indicating member 314 is illustrated as having eight (8) feet members 346 spaced apart, preferably evenly spaced apart, and arranged about the perimeter. Such number and arrangement is illustrative and can be modified, both in number and orientation/placement as needed. The size, shape, and length extending outward are designed to allow the feet member 346 to prevent or minimize surface tension with any liquid interactions.

The second indicating member main body 336 may also contain one or more elongated protuberances, ribs, or raised surfaces with a defined size and shape 354. The one or more elongated protuberances or ribs 354 may contain a body 356 that extends into the feet member body 348. The feet member body 348 and the elongated protuberances or ribs body 356 may be separated by a stepped surface 356. The stepped surfaces 356 allow the second indicating member main body 336 to seat properly and avoid the drain plug 1109. Alternatively, the one or more elongated protuberances or ribs 354 may be separate from the feet members 346. The second indicating member 314 is illustrated as having eight (8) elongated protuberances or ribs 354 spaced apart, preferably evenly spaced apart, and arranged about the perimeter. Such number and arrangement is illustrative and can be modified, both in number and orientation/placement as needed. A plurality of second elongated bodies 358, shown having an elongated and cylindrical shaped body, are the result of the process of molding the second indicating member 314.

Figure 34:
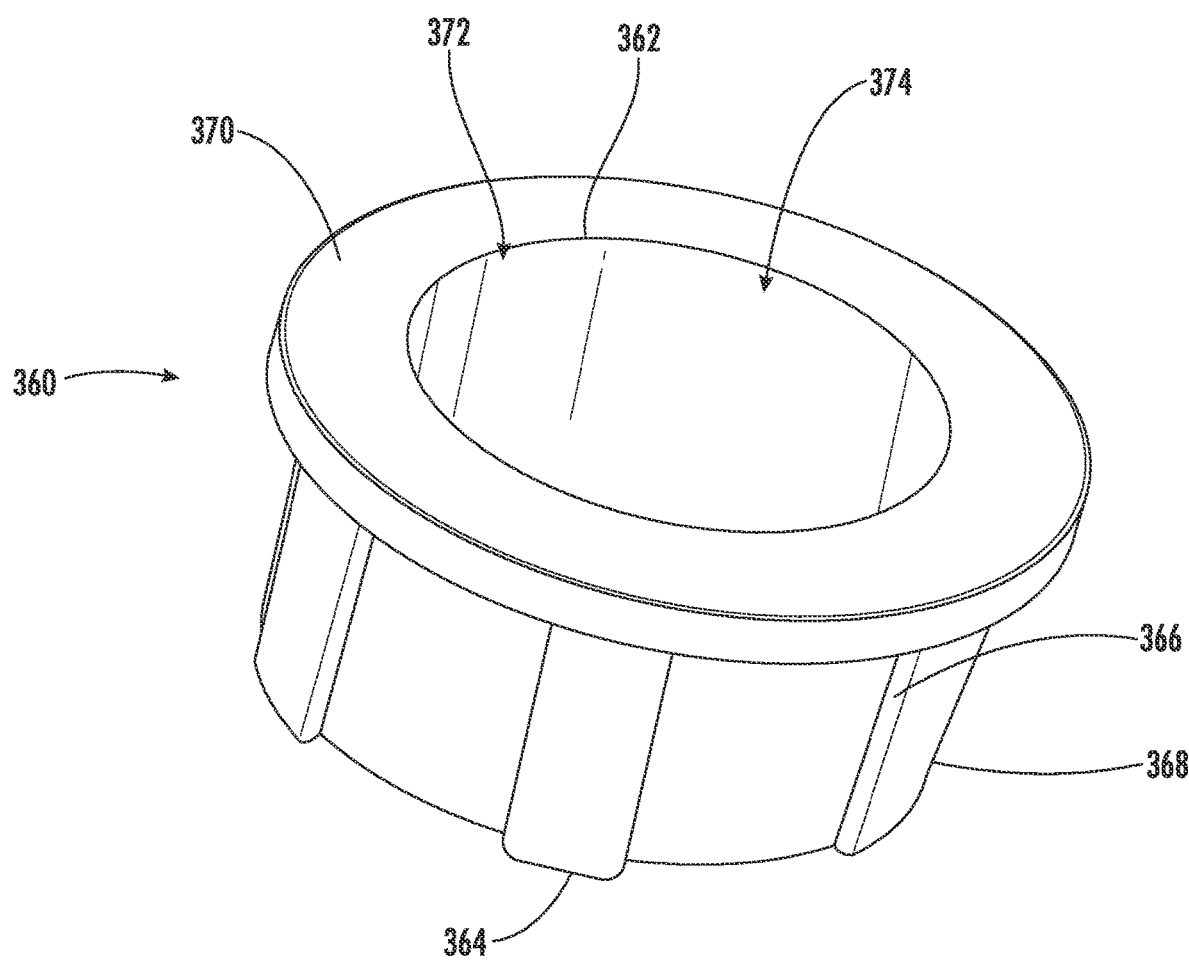
FIG. 34 is a perspective view of an illustrative stopper or stop member.

The fuel indicator 300 may include the use of a stopper or stopping member 360, see FIG. 34. The stopper or stopping member 360 may include a first end 362, an opposing second end 364, and a main body 366. The stopper or stopping member 360 may be sized and shaped to interact with the second indicating member 314, preventing the second indicating member 314 from moving "or floating" into the fuel filter 1100.

Figure 29:
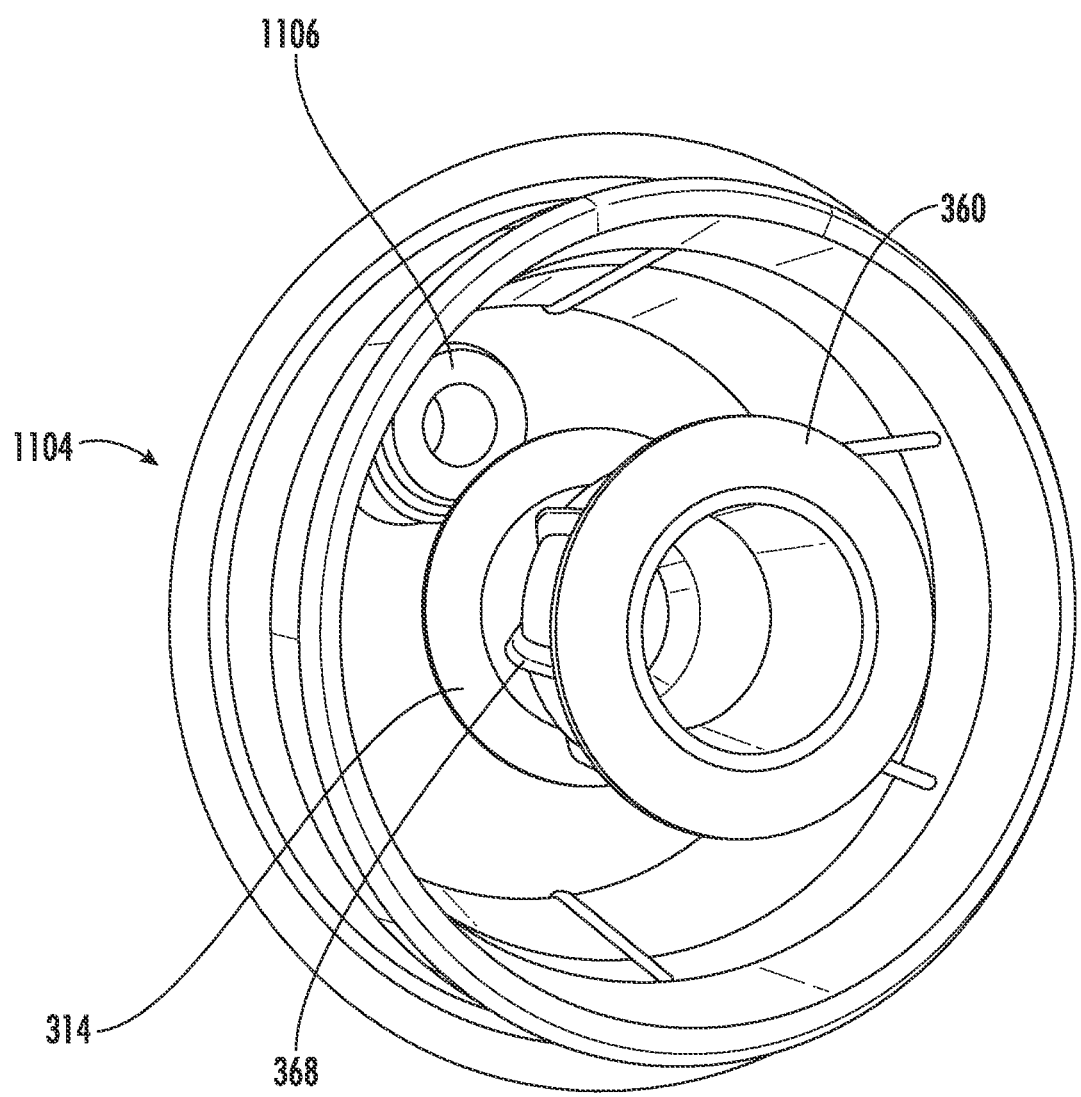
FIG. 29 is a top view of the separated fuel filter bowl.

In the situation where the second indicating member 314 floats up into the filter (in quick flood case), the results may case the sensor to activate only once, i.e. cause a single signal of light and/or sound, and then stop signaling. Once the signal stops, the user may not realize water is entering the fuel. The main body 366 may include fins or protuberances 368, see also FIG. 29, spaced apart, preferably evenly spaced apart, and arranged about the perimeter. The main body 366 may also contain a flange or surface 370 at, and encircling, the first end 362. The flange or surface 370 extends out and away from the main body 366. The main body 366 preferably includes an opening 372, exposing an interior 374. The opening 372 is sized and shaped to allow the stopper or stopping member 360 to fit over a portion of the fuel filter 1100, preferably the elongated structure 1105.

Figure 35:
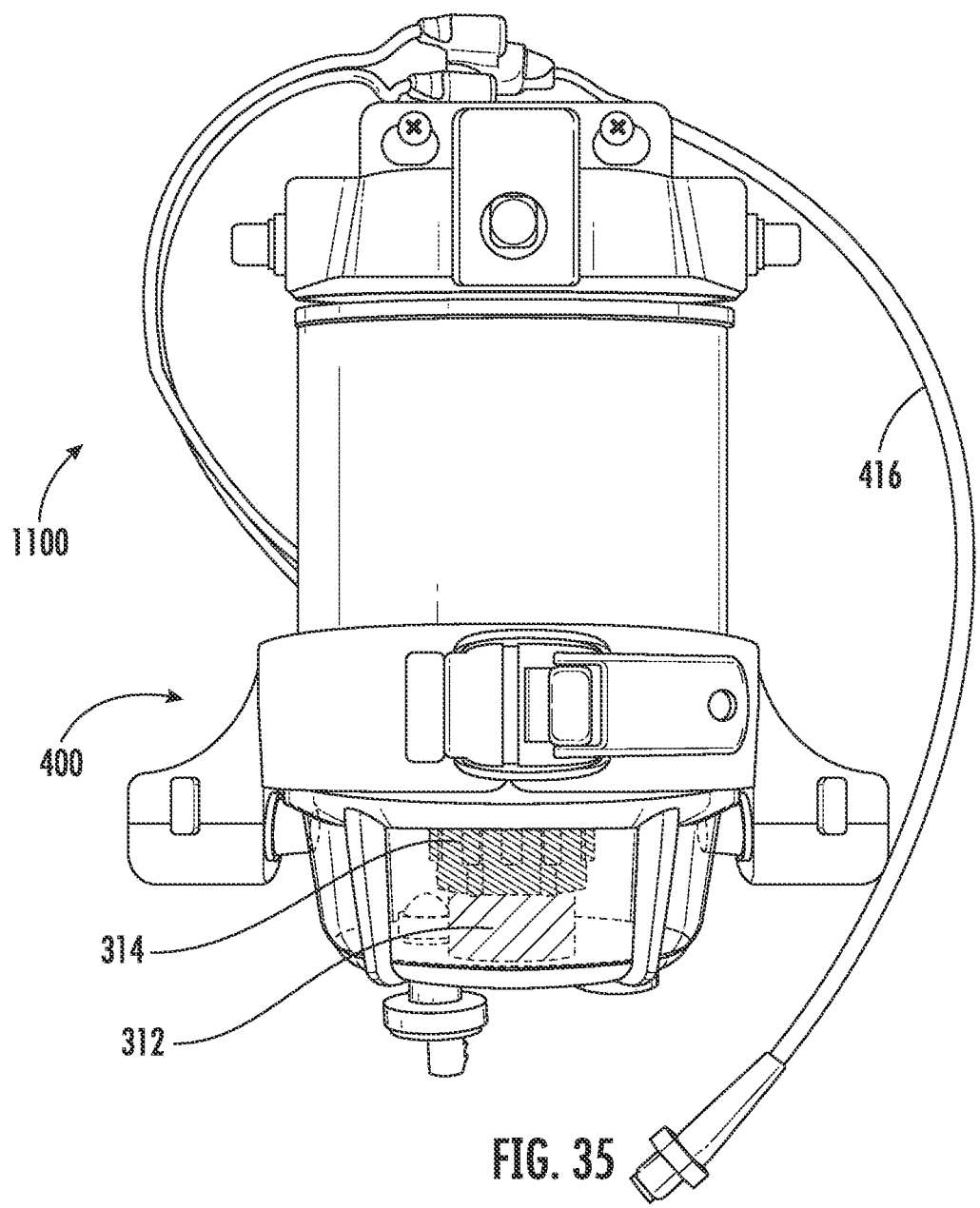
FIG. 35 illustrates a fuel filter shown with the fuel quality indicator device and remote alert system.

Referring to FIG. 35, the fuel filter water separator 1100, with fuel indicator device 300, is shown with a remote alert system 400. The remote alert system 400 is similar to the remote alert system 200 and has the same functionality.

Figure 36:
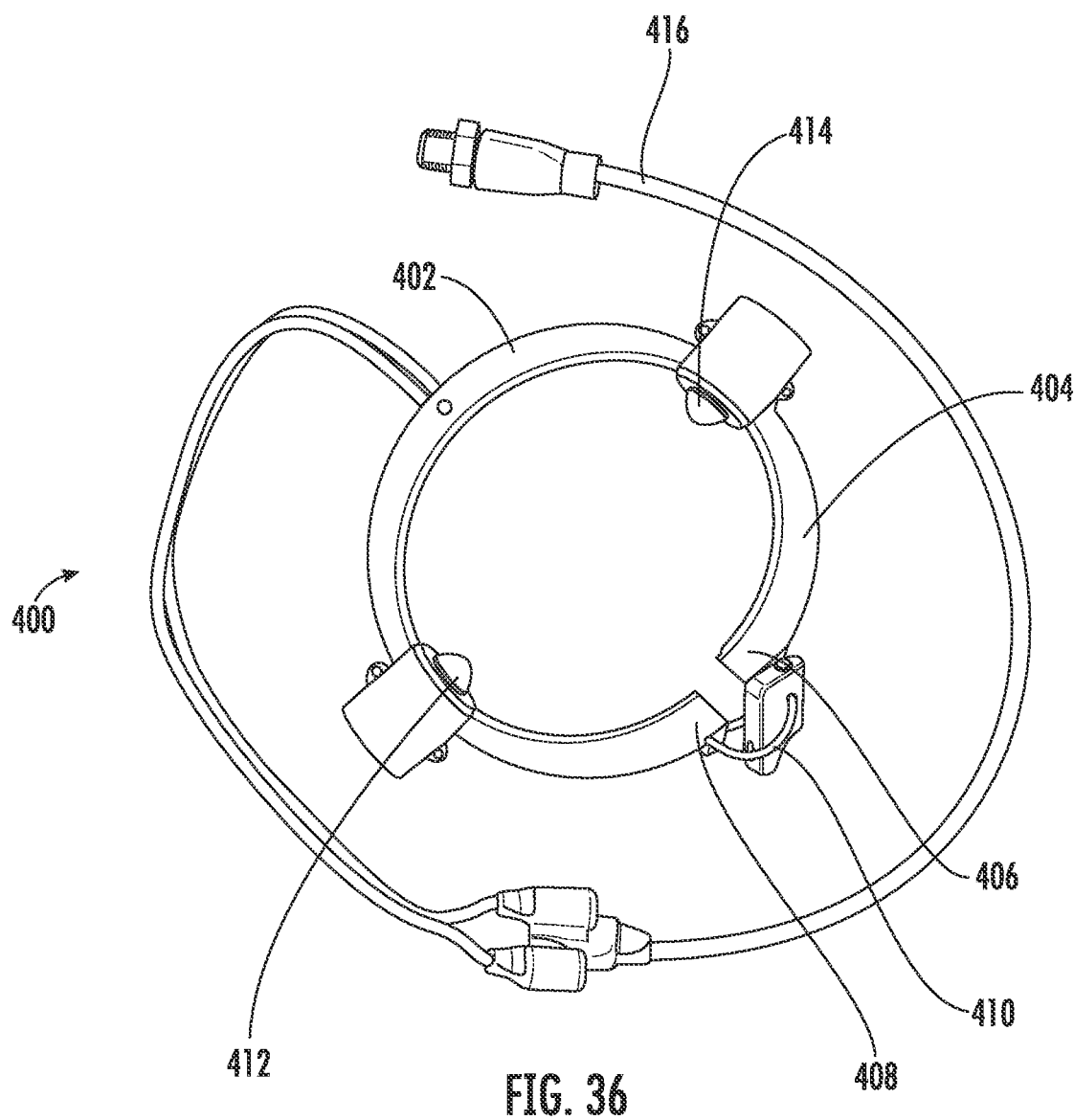
FIG. 36 is a top view of an illustrative example of a remote alert system.
Figure 37:
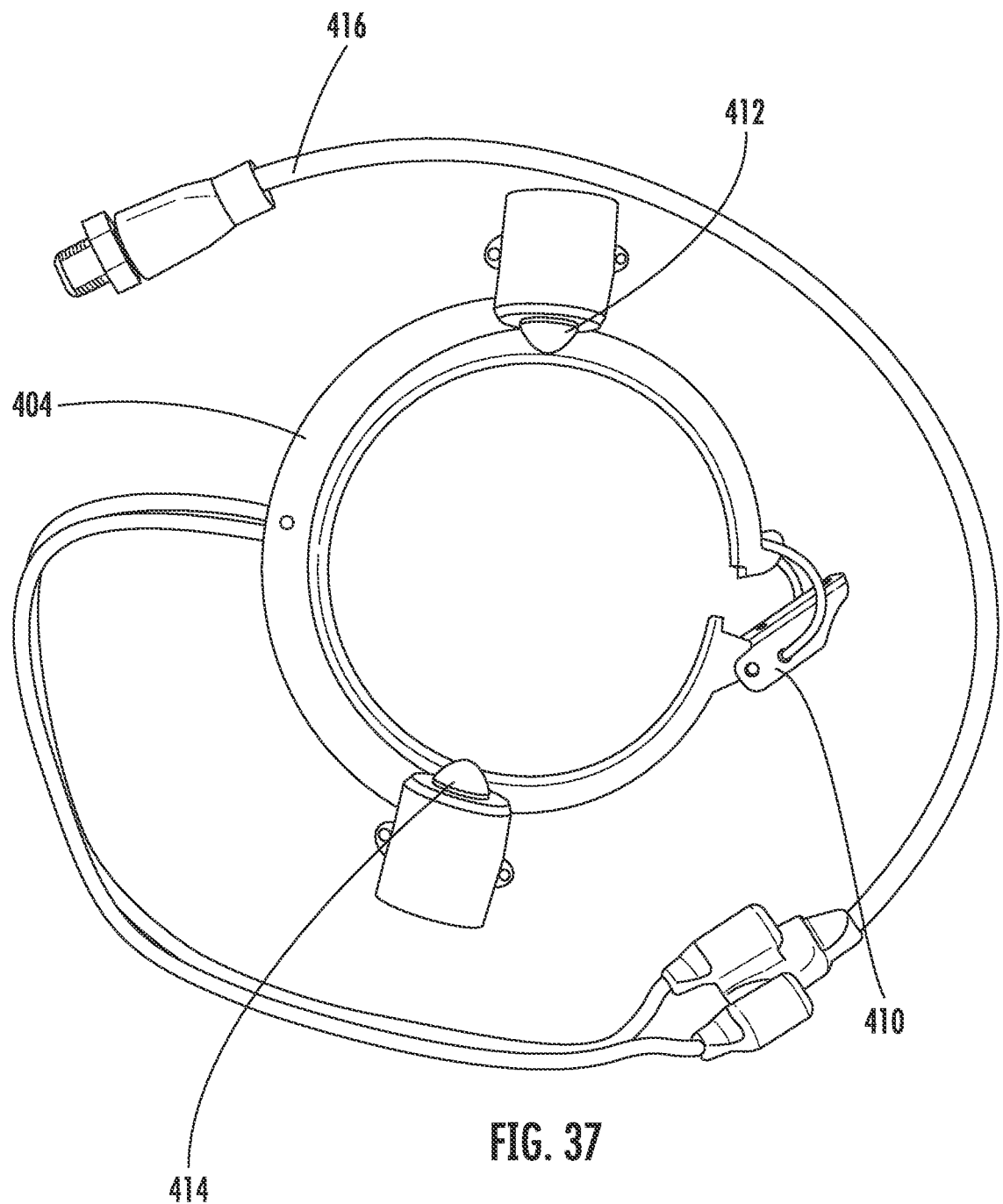
FIG. 37 is a bottom view of an illustrative example of a remote alert system.
Figure 38:
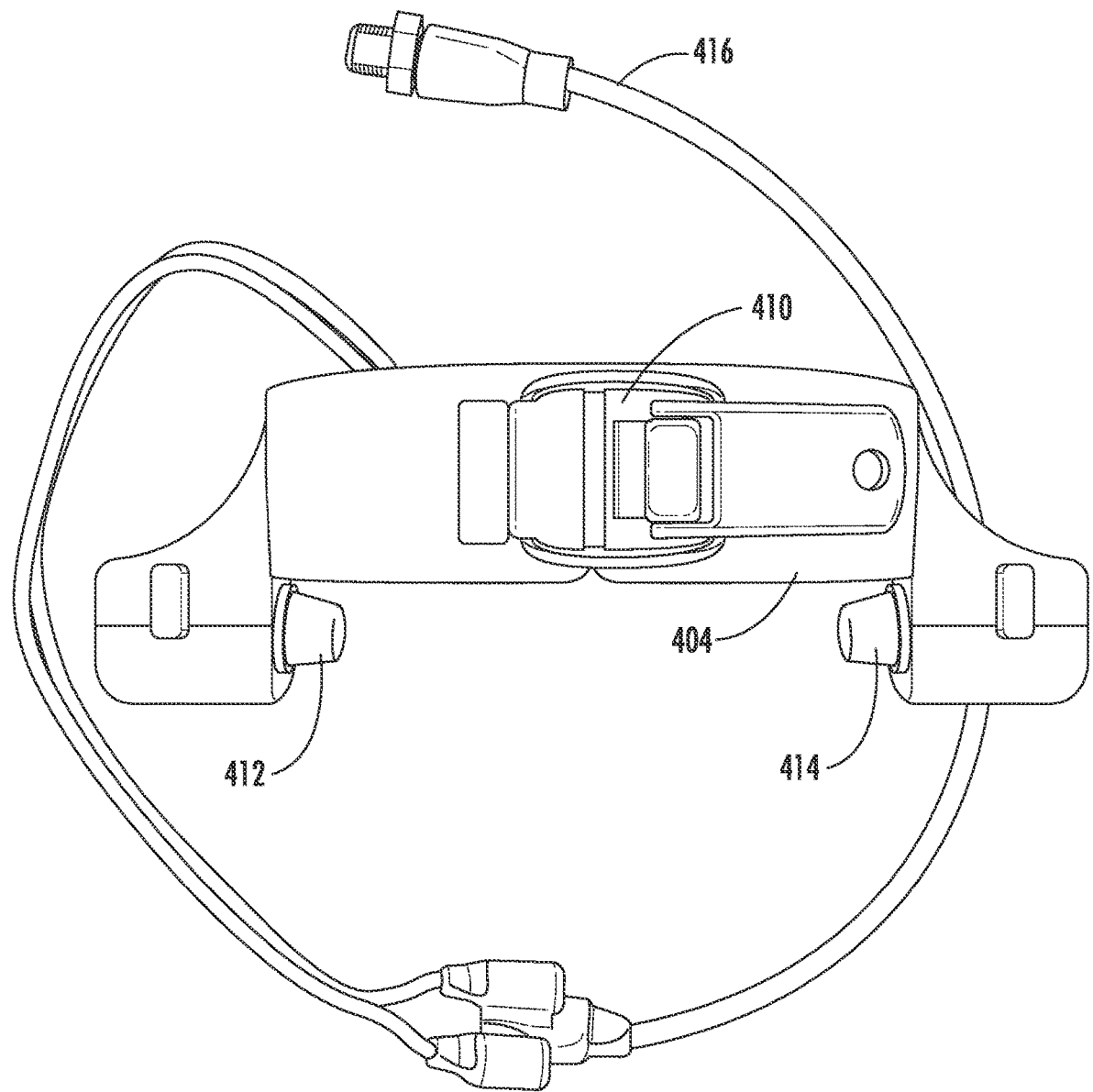
FIG. 38 is a side view of an illustrative example of a remote alert system.

The remote alert system 400 is designed as an additional alert mechanism to indicate the presence of water within the fuel. FIGS. 36-38 illustrate the remote alert system 400 removed from the fuel filter 1100. The remote alert system 400 may comprise a fuel quality indicator device remote alert attachment member 402. The fuel quality indicator device remote alert attachment member 402 comprises a main body 404 having a first end 406 securable to a second end 408 via a securing mechanism known to one of skill in the art, such as via buttons, chemical fastening such as glue, hook and loop fastening such as VELCRO, and buckles. As illustrated, the securing mechanism is a clasp lock 410. The main body 404 may be constructed of a stretchable or flexible material, such as a plastic material. The remote alert system 400 may comprise a first sensor 412, preferably a photo emitting/sending sensor, and a second sensor 414, preferably a photo detecting/receiving sensor. The first sensor 412 and the second sensor 414 are preferably spaced apart and aligned so that the second sensor 414 detects or receives an electromagnetic radiation signal, such as a laser or LED beam generated from the first sensor 412.

Alternatively, the first sensor 412 and the second sensor 414 may be secured to the main body 404 and aligned so that the second sensor 414 detects or receives an electromagnetic radiation signal, such as a laser or LED beam, generated from the first sensor 412.

Figure 40:
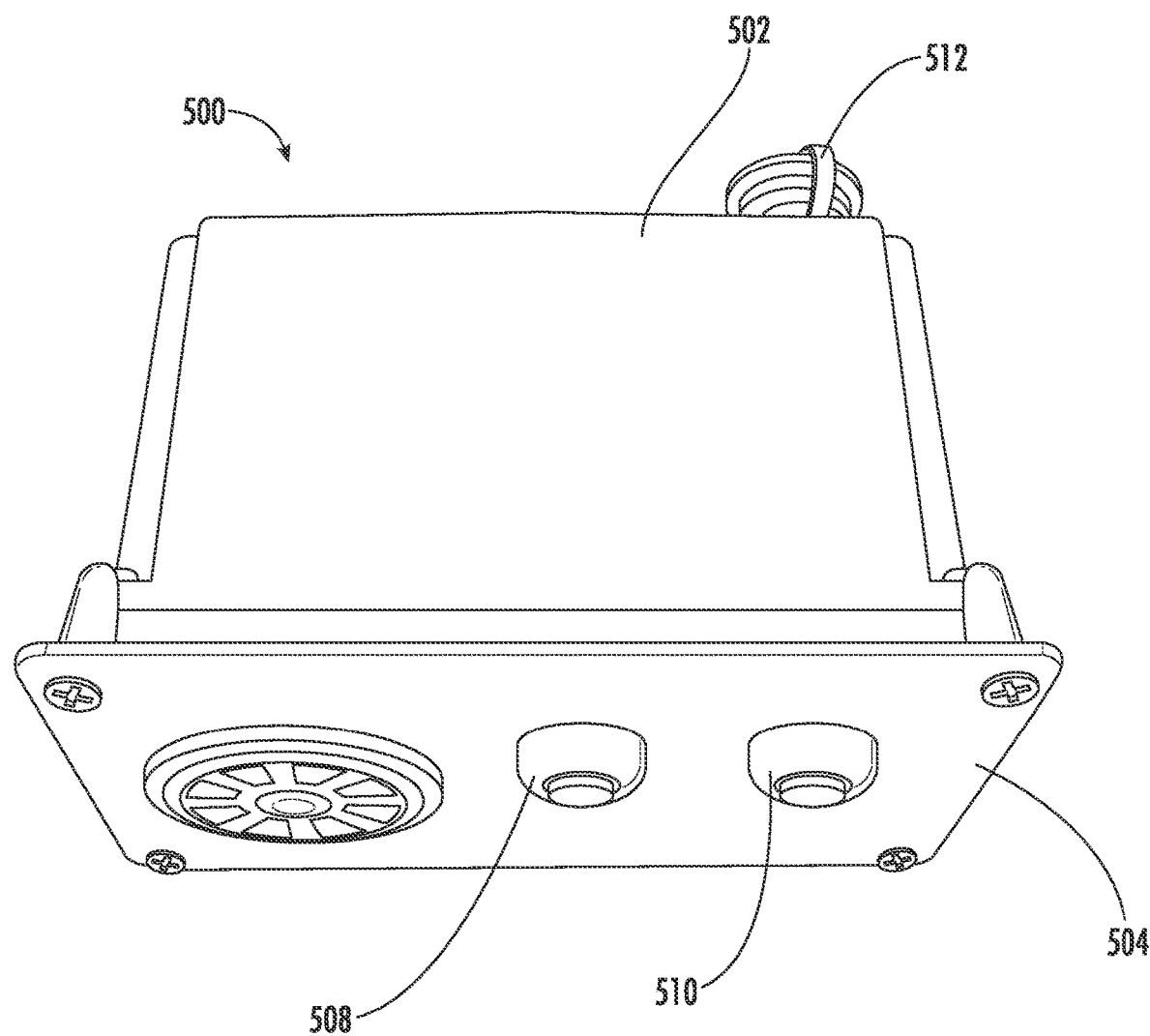
FIG. 40 is an illustrative example of an indicator or alerting device.
Figure 41:
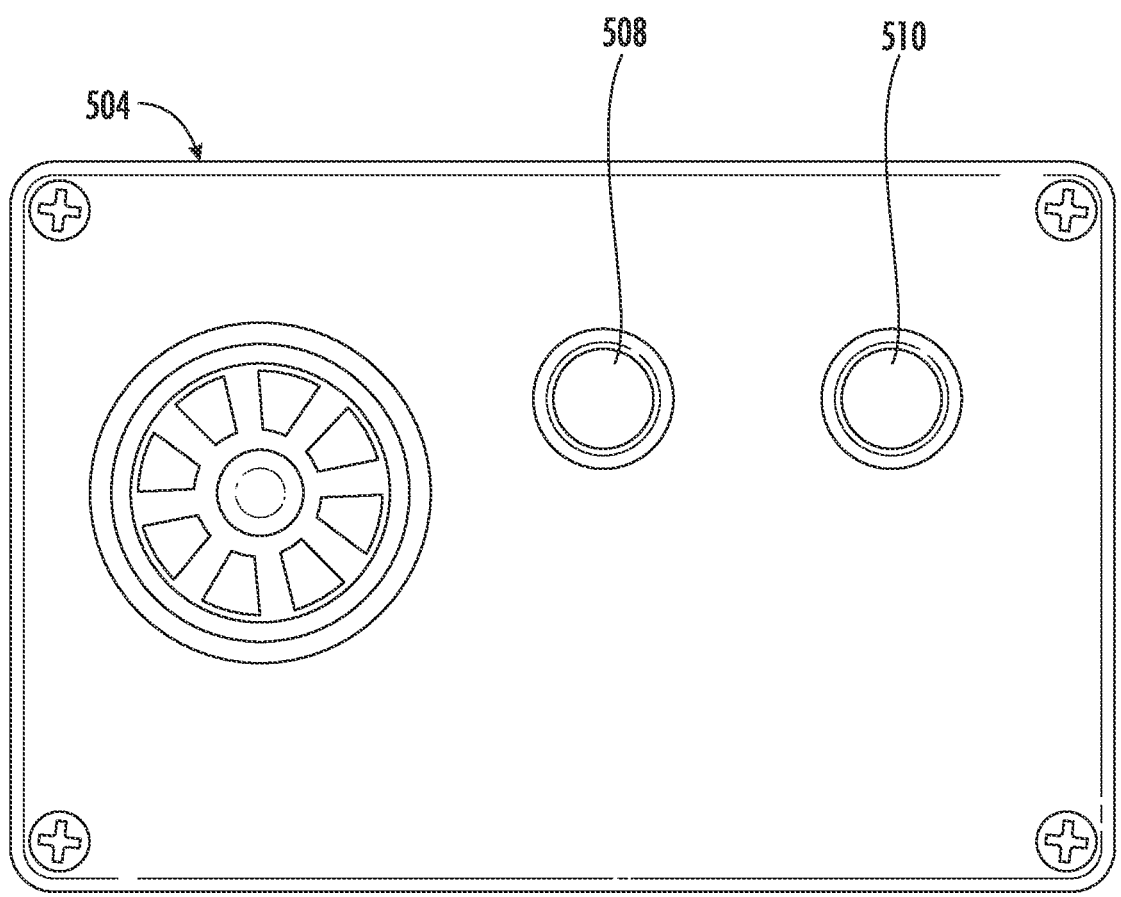
FIG. 41 illustrates a display panel of the indicator or alerting device.

The fuel quality indicator device remote alert attachment member 402 is operatively connected to an indicator or alerting device 500, via wires or wirelessly via, for example, WIFI or BLUETOOTH technology. The indicator or alerting device 500 is configured to provide an alert via, for example, production of sound, lights, or other mechanisms known to one of skill in the art. Referring to FIG. 40, an illustrative example of an indicator or alerting device 500 is shown. The indicator or alerting device 500 may include a housing unit 502. The housing unit 502 is designed to house and store one or more functional structures, including any electronics, electronics receptacles, wires, lights, batteries (if used), or circuit boards, that drive functionality. The housing unit 502 may include a front panel 504, see FIG. 41, having a general indicator light 506 and one or more individual sensor indicator lights 508 and 510. The general indicator light 506 may be designed to flash or blink (and/or produce sound) when the sensors are activated, i.e. as a result of water in the motor, caused by the second indicating member 314 moving about the first indicating member 312. The individual sensor indicator lights 508 and 510 may be designed to alert, i.e. flash or blink, (and/or produces sound) the user as to which fuel indicator device 300 is being activated if the user is using a machine, i.e. boat, having multiple motors. The indicator or alerting device 500 is operatively connected to the remote alert system 400 via sensor wires 416 being plugged into an electrical receptacle 512.

Figure 39:
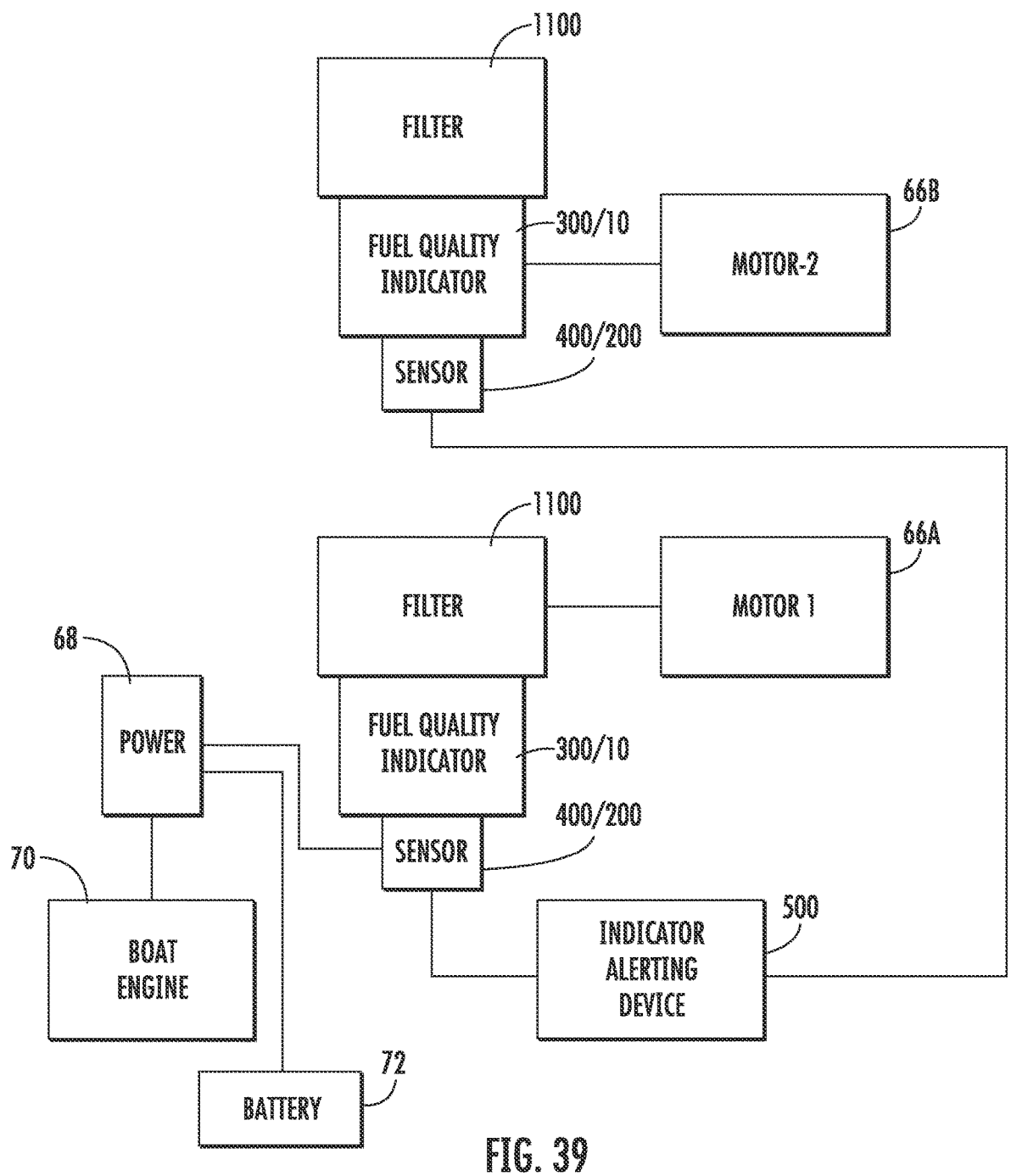
FIG. 39 is a schematic drawing illustrating the operative connection between the fuel quality indicator device, fuel filter water separator, remote alert system, motor, and power source.

In use, the fuel indicator device 300, with remote alert system 400 is operatively connected to a boat motor(s) 66A through the fuel filter 1100, see FIG. 39. The alert system 400 may be wired (or operate wirelessly) to 1) the indicator or alerting device 500, and to 2) a power source 68. Preferably, the power source 68 is a boat engine 70. The alert system 400 being hardwired to the boat engine is the preferred source of power so as to prevent false readings, i.e. the power source is not turned on or has run out of power (if using a battery 72). Accordingly, when the boat is powered, the alert system 400 will be powered. The alert system 400 may be configured with a "ON" or "OFF" button to power the system on or off. As shown in FIG. 39, a boat may use multiple the fuel indicator devices 300, each secured or operatively connected to independent motors, motor-1, 66A or second (or third, fourth, etc.), independent motor-2, 66B.

In accordance with the embodiments of the invention, one or more of the individual components or structures may be form part of a kit.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A fuel quality indicator for use in indicating presence of water within a fuel source, comprising:
   a first fuel quality indicator member having an outer surface comprising a first visual indicator for visually indicating a presence of water in a fuel source; and
   a second fuel quality indicator member having an outer surface comprising a second visual indicator for visually indicating an absence of water in said fuel source, and constructed and arranged to float in the presence of water and sink in the presence of said fuel source, said second visual indicator outer surface being different than said first visual indicator outer surface;
   wherein said first fuel quality indicating member and said second fuel quality indicating member are co-axially aligned, with said second fuel quality indicating member positioned over and oriented around said first fuel quality indicator.

2. The fuel quality indicator for use in indicating presence of water within a fuel source according to claim 1,
   wherein said first fuel quality indicator member is constructed and arranged to engage with a portion of a fluid collecting canister; and
   said second fuel quality indicator member is constructed and arranged to movably engage with said portion of a fuel filter fluid collecting canister engaged with said first fuel quality indicator member, wherein said second fuel quality indicator member is traversable from a first position to at least a second position in the presence of water.

3. The fuel quality indicator for use in indicating presence of water within a fuel source according to claim 1, wherein said first visual indicator and said second visual indicator include words, letters, symbols, pictures, colors, or combinations thereof.

4. The fuel quality indicator for use in indicating presence of water within a fuel source according to claim 1, wherein said second fuel quality indicator member has a specific gravity of less than 1.0.

5. The fuel quality indicator for use in indicating presence of water within a fuel source according to claim 4, wherein said second fuel quality indicator member has a specific gravity of between 0.75 and less than 1.0.

6. The fuel quality indicator for use in indicating presence of water within fuel source according to claim 5, wherein said second fuel quality indicator member has a specific gravity in the range of 0.9 or 0.95.

7. A system for detecting the presence of water within a fuel source, comprising:
   a fuel quality indicator comprising:
      a first indicator member having an outer surface comprising a first visual indicator for visually indicating a presence of water in a fuel source;
      a second indicator member having an outer surface comprising a second visual indicator for visually indicating an absence of water in said fuel source, and constructed and arranged to float in the presence of water and sink in the presence of said fuel source, said second visual indicator outer surface being different than said first visual indicator outer surface;
      wherein said first indicating member and said second indicating member are co-axially aligned, with said second indicating member positioned over and oriented around said first indicator;
   a secondary alert system for indicating the presence of water within the fuel comprising a first sensor and a second sensor, said first sensor and said second sensor operatively coupled to movement of said second indicator member.

8. The system for detecting the presence of water within a fuel source according to claim 7, wherein said fuel quality indicator includes a stop member.

9. The system for detecting the presence of water within a fuel source according to claim 7, wherein said alert system includes fuel quality indicator device remote alert attachment member.

10. The system for detecting the presence of water within a fuel source according to claim 7, further including a housing unit having a panel comprising one or more lights operatively connected to said first and second sensors.

11. The system for detecting the presence of water within a fuel source according to claim 10, wherein said housing unit having a panel is constructed and arranged to produce one or more sounds.

12. The system for detecting the presence of water within a fuel source according to claim 7, wherein said first indicator member is constructed and arranged to engage with a portion of a fluid collecting canister; and
   said second indicator member is constructed and arranged to movably engage with said portion of a fuel filter canister engaged with said firs indicator member, wherein said second indicator member is traversable from a first position to at least a second position, and said first member indicator is in a fixed position.

13. The system for detecting the presence of water within a fuel source according to claim 7, wherein said first visual indicator and said second visual indicator include words, letters, symbols, pictures, colors, or combinations thereof.

14. The system for detecting the presence of water within a fuel source according to claim 7, wherein aid second indicator member has a specific gravity of less than 1.0.

15. The system for detecting the presence of water within a fuel source according to claim 7, wherein said second indicator member has a specific gravity of between 0.75 and less than 1.0.

* * * * *